US007678569B2

(12) United States Patent
Bukh et al.

(10) Patent No.: US 7,678,569 B2
(45) Date of Patent: Mar. 16, 2010

(54) CLONED GENOME OF INFECTIOUS HEPATITIS C VIRUS STRAIN HC-TN AND USES THEREOF

(75) Inventors: Jens Bukh, Praesto (DK); Robert H. Purcell, Gaithersburg, MD (US); Suzanne U. Emerson, Darnestown, MD (US); Akito Sakai, Ishikawa (JP)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 12/061,504

(22) Filed: Apr. 2, 2008

(65) Prior Publication Data

US 2009/0252755 A1 Oct. 8, 2009

(51) Int. Cl.
*C12N 15/00* (2006.01)
*C12N 7/00* (2006.01)
*C12P 21/00* (2006.01)
*C07H 21/00* (2006.01)

(52) U.S. Cl. ............... 435/320.1; 536/23.1; 536/23.72; 435/235.1; 435/69.1

(58) Field of Classification Search ...................... None
See application file for complete search history.

(56) References Cited

OTHER PUBLICATIONS

Kato et al., "Production of Infectious Hepatitis C Virus of Various Genotypes in Cell Cultures," Journal of Virology, vol. 81 No. 9, pp. 4405-4411 (Epub Feb. 2007).*
GenBank AF100207.1, "Hepatitis C virus clone C14-106 polyprotein gene, partial cds.," Jun. 1999.*
Sakai et al., "In Vivo study of the HC-TN Strain of Hepatitis C Virus Recovered from a Case of Fulminant Hepatitis: RNA Transcripts of a Molecular Clone (pHC-TN) are Infectious in Chimpanzees but not in Huh7.5 cells," Journal of Virology, vol. 81 No. 13, pp. 7208-7219 (2007).*
Allander, T., et al., 1997 Patients infected with the same hepatitis C virus strain display different kinetics of the isolate-specific antibody response, *J. Infect. Dis.* 175:26-31.
Alter, M.J. 1997 Epidemiology of hepatitis C *Hepatology* 26:62S-65S.
Bartosch, B., et al., 2003 In vitro assay for neutralizing antibody to hepatitis C virus: evidence for broadly conserved neutralization epitopes, *Proc. Natl. Acad. Sci. USA* 100:14199-14204.
Blight, K.J. and Rice, C.M. 1997 Secondary structure determination of the conserved 98-base sequence at the 3' terminus of hepatitis C virus genome RNA *J. Virol.* 71:7345-7352.
Bouchard M. J., et al., 1995 Determinants of attenuation and temperature sensitivity in the type 1 poliovirus Sabin vaccine. *J. Virol.* 69:4972-4978.
Bukh, J. 2004 A critical role for the chimpanzee model in the study of hepatitis C, *Hepatology* 39:1469-1475.
Bukh, J., et al., 1993 At least 12 genotypes of hepatitis C virus predicted by sequence analysis of the putative E1 gene of isolates collected worldwide *PNAS USA* 90:8234-8238.
Bukh, J., et al., 1998 Experimental infection of chimpanzees with hepatitis C virus of genotype 5a: genetic analysis of the virus and generation of a standardized challenge pool, *J. Infect. Dis.* 178:1193-1197.
Bukh, J., et al., 2002 Monoclonal Hepatitis C Virus Infection In Chimpanzees in H. S. Margolis, M. J. Alter, T. J. Liang, and J. L. Dienstag (ed.), Viral hepatitis and liver disease. International Medical Press, Atlanta, GA; 10th International Symposium on Viral Hepatitis and Liver Disease pp. 345-349.
Bukh, J. et al. 2002 Analysis of the Hypervariable Region 1 of Hepatitis C Virus *In* H. S. Margolis, M. J. Alter, T. J. Liang, and J. L. Dienstag (ed.), Viral hepatitis and liver disease. International Medical Press, Atlanta, GA; 10th International Symposium on Viral Hepatitis and Liver Disease pp. 347-352.
Bukh, J., et al., 2002 Mutations that permit efficient replication of hepatitis C virus RNA in Huh-7 cells prevent productive replication in chimpanzees, *Proc. Natl. Sci. USA* 99:14416-14421.
Bukh, J., et al., 1995 Genetic heterogeneity of hepatitis C virus: quasispecies and genotypes, *Semin. Liver Dis.* 15:41-63.
Choo, Q. L., et al., 1991 Genetic organization and diversity of the hepatitis C virus *Proc. Natl. Acad. Sci. USA* 88:2451-2455.
Cooper, S., et al., 1999 Analysis of a successful immune response against hepatitis C virus *Immunity* 10:439-449.
Davis, G.L., et al., 1998 Interferon alfa-2b alone or in combination with ribavirin for the treatment of relapse of chronic hepatitis C *N. Engl. J. Med.* 339:1493-1499.
Erickson, A. L., et al., 2001 The outcome of hepatitis C virus infection is predicted by escape mutations in epitopes targeted by cytotoxic T lymphocytes *Immunity* 15:883-895.
Farci, P., et al., 1996 Hepatitis C virus-associated fulminant hepatic failure *N. Engl. J. Med.* 335:631-634.
Farci, P., et al., 1999 Experimental transmission of hepatitis C virus-associated fulminant hepatitis to a chimpanzee *J. Infect. Dis.* 179:1007-1011.
Farci, P., et al., 2000 The outcome of acute hepatitis C predicted by the evolution of the viral quasispecies *Science* 288:339-344.
Feinstone, S. M., et al., 1981 Non-A, non-B hepatitis in chimpanzees and mermosets *J. Infect. Dis.* 144:588-598.
Forns, X. and Bukh, J. 1998 Methods for determining the hepatitis C virus genotype *Viral Hepatitis Reviews* 4:1-19.
Forns, X., et al. 2000 Hepatitis C virus lacking the hypervariable region 1 of the second envelope protein is infectious and causes acute resolving or persistent infection in chimpanzees *Proc. Natl. Acad. Sci. USA* 97:13318-13323.
Grakoui, A., et al., 1993 Expression and identification of hepatitis C virus polyprotein cleavage products *J. Virol* 67:1385-1395.
Han, J. H., et al., 1991 Characterization of the terminal regions of hepatitis C viral RNA: Identification of conserved sequences in the 5' untranslated region and poly(A) tails at the 3' end *Proc. Natl. Acad. Sci. USA* 88:1711-1715.

(Continued)

*Primary Examiner*—Zachariah Lucas
(74) *Attorney, Agent, or Firm*—Knobbe, Martens, Olson & Bear, LLP; Eric Furman

(57) ABSTRACT

Embodiments described herein include nucleic acid sequences, which encode hepatitis C virus of strain HC-TN, genotype 1a, proteins and polypeptides and fragments thereof. Use of these compositions, and diagnostics for HCV and in the development of screening assays for the identification of antiviral agents for HCV are also contemplated.

7 Claims, 17 Drawing Sheets

OTHER PUBLICATIONS

Hijikata, M., et al., 1991 Hypervariable regions in the putative glycoprotein of hepatitis C virus *Biochem. Biophys. Res. Commun.* 175:220-228.

Honda, M., et al. 1996 Stability of a stem-loop involving the initiator AUG controls the efficiency of internal initiation of translation of hepatitis C virus RNA, *RNA* 2:955-968.

Hoofnagle, J. H., 1997 Hepatitis C: the clinical spectrum of disease *Hepatology* 26:15S-20S.

Houghton, M. 1996 Hepatitis C viruses. In *Fields Virology* (B. N. Fields, D. M. Knipe, P. M. Howley, et al., Eds.), Third ed., pp. 1035-1058. Lippincott-Raven Publishers, Philadelphia, Fig. 1; and Major, M.E. et al. (1997), Table 2.

Ito, T. and Lai, M.M. C. 1997 Determination of the secondary structure of and cellular protein binding to the 3'-untranslated region of the hepatitis C virus RNA genome *J. Virol.* 71:8698-8706.

Kato, T., et al., 2001 Sequence analysis of hepatitis C virus isolated from a fulminant hepatitis patient *J. Med. Virol.* 64:334-339.

Kolykhalov, A. A., et al., 1997 Transmission of hepatitis C by intrahepatic inoculation with transcribed RNA *Science* 277:570-574.

Kolykhalov, A, A., et al., 2000 Hepatitis C virus-encoded enzymatic activities and conserved RNA elements in the 3' nontranslated region are essential for virus replication in vivo *J. Virol.* 74:2046-2051.

Kolykhalov, A.A., et al., 1996 Identification of a highly conserved sequence element at the 3' terminus of hepatitis C virus genome *J. Virol.* 70:3363-3371.

Kumar, U., et al., 2000 Sequence, expression and reconstitution of an HCV genome from a British isolate derived from a single blood donation *J. Viral Hepat.* 7:459-465.

Lechner, F., et al., 2000 Analysis of successful immune responses in persons infected with hepatitis C virus *J. Exp. Med.* 191:1499-1512.

Lesniewski, R. R., et al., Expression of HCV envelope proteins and the serological utility of the anti-E2 immune response 1995 *Princess Takamatsu Symp.* 25:129-137.

Lin, C., et al., 1994 Processing in the hepatitis C virus E2-NS2 region: identification of p7 and two distinct E2-specific products with different C termini *J. Virol.* 68:5063-5073.

Major, M. E., et al., 1999 Long-term follow-up of chimpanzees inoculated with the first infectious clone for hepatitis C virus *J. Virol.* 73:3317-3325.

Major, M. E., et al., 2004 Hepatitis C virus kinetics and host responses associated with disease and outcome of infection in chimpanzees *Hepatology* 39:1709-1720.

McHutchison, J.G., et al., 1998 Interferson Alfa-2b alone or in combination with ribavirin as initial treatment for chronic hepatitis C *N. Engl. J. Med.* 339:1485-1492.

Meunier, J. C., et al., 2005 Evidence for cross-genotype neutralization of hepatitis C virus pseudo-particles and enhancement of infectivity by apolipoprotein C1 *Proc. Natl. Acad. Sci. USA* 102:4560-4565.

Muto, Y., et al., 1990 Anti-hepatitis C virus antibody prevails in fulminant hepatic failure *Gastroenterol. Jpn.* 25:32-35.

Nakao, H., et al., 1996 Full-length genomic sequence of a hepatitis C virus genotype 2c isolate (BEBEI) and the 2c-specific PCR primers *Arch. Virol.* 141:701-704.

Navaneetham, D. and Conti-Fine, B.M. 1998. "Augmented PCR amplification by thermally activated DNA polymerase—AmplTaq Gold, in the presence of densifying agents" printed from internet site "http://astro.temple.edu".

Okamoto, H., et al., 1992 Full-length nucleotide sequence of a Japanese hepatitis C virus isolate (HC-J1) with high homology to US isolates *Nucleic Acids Res.* 20:6410.

Okamoto, H., et al., 1992 Full-length sequence of a hepatitis C virus genome having poor homology to reported isolates: comparative study of four distinct genotypes *Virology* 188:331-341.

Rice, C.M. 1996 Flaviviridae: The viruses and their replication, In *Fields Virology* (B. N. Fields, D. M. Knipe, P. M. Howley, et al., Eds.), Third ed., pp. 931-959. Lippincott-Raven Publishers, Philadelphia).

Seeff, L. B. ,et al., 2001 Long-term mortality and morbidity of transfusion-associated non-A, non-B, and type C hepatitis : a National Heart, Lung, and Blood Institute collaborative study *Hepatology* 33:455-463.

Sharp, M., et al., 1988 Codon usage patterns in *Escherichia, coli, Bacillus subtilis, Saccharomyces cerevisiae, Schizosaccharomyces pombe, Drosophila melanogaster,* and *Homo sapiens*; a review of the considerable within-species diversity *Nucleic Acids Res.* 16:8207-11.

Shata, M. T., et al., 2003 Exposure to low infective doses of HCV induces cellular immune responses without consistently detectable viremia or seroconversion in chimpanzees *Virology* 314:601-616.

Simmonds, P., et al., 1993 Classification of hepatitis C virus into six major genotypes and a series of subtypes by phylogentic analysis of the NS-5 region *J. Gen. Virol.* 74:2391-2399.

Su, A. I., et al., 2002 Genomic analysis of the host response to hepatitis C virus infection *Proc. Natl. Acad. Sci. USA* 99:15669-15674.

Tanaka, T., et al., 1995 A novel sequence found at the 3' terminus of hepatitis C virus genome *Biochem. Biophys. Res. Commun.* 215:744-749.

Tanaka, T., et al., 1996 Structure of the 3' terminus of the hepatitis C virus Genome *J. Virol.* 70:3307-3312.

Thimme, R., et al., 2001 Determinants of viral clearance and persistence during acute hepatitis C infection *J. Exp. Med.* 194:1395-1406.

Thimme, R., et al., 2002 Viral and immunological determinants of hepatitis C virus clearance, persistence, and disease *Proc. Natl. Acad. Sci. USA* 99:15661-15668.

Thomson, M., et al., 2001 Emergence of a distinct pattern of viral mutations in chimpanzees infected with a homogeneous inoculum of hepatitis C virus *Gastroenterology* 121:1226-1233.

Tsuchihara, K., et al., 1997 Specific Interaction of polypyrimidine tract-binding protein with the extreme 3'-terminal structure of the hepatitis C virus genome, the 3'30 *J. Virol.* 71:6720-6726.

Tsukiyama-Kohara, K. et al. 1992 *J. Virol.* 66:1476-1483; Honda, M., et al. 1996 *RNA* 2:955-968.

Wakita, T., et al., 2005 Production of infectious hepatitis C virus in tissue culture from blood a cloned viral genome *Nat. Med.* 11:791-796.

Weiner, A. ,et al., 1995 Persistent hepatitis C virus infection in a chimpanzee is associated with emergence of a cytotoxic T lymphocyte escape variant *Proc. Natl. Acad. Sci. USA* 92:2755-2759.

Weiner, A.J., et al., 1991 Variable and hypervariable domains are found in the regions of HCV corresponding to the flavivirus envelope and NS1 proteins and the pestivirus envelope glycoproteins *Virology* 180:842-848.

Wright, T. L, et al., 1991 Hepatitis C virus not found in fulminant non-A, non-B hepatitis *Ann. Intern. Med.* 115:111-112.

Yamada, N., et al. 1996, Genetic Organization and Diversity of the 3' Noncoding Region of the Hepatitis C Virus Genome, *Virology* 223:255-261.

Yanagi et al., 1997 Transcripts from a single full-length cDNA clone of hepatitis C virus are infectious when directly transfected into the liver of a chimpanzee *PNAS USA* 94:8738-8743.

Yanagi, M., et al., 1991 Hepatitis C virus in fulminant hepatic failure *N. Engl. J. Med.* 324:1895-1896.

Yanagi, M., et al., 1998 Transcripts of a chimeric cDNA clone of hepatitis C virus genotype 1b are infectious in vivo *Virology* 244:161-172.

Yanagi, M., et al., 1999 Hepatitis C virus: an infectious molecular clone of a second major genotype (2a) and lack of viability of intertypic 1a and 2a chimeras *Virology* 262:250-263.

Yi, M., et al., 2006 Production of infectious genotype 1a hepatitis C virus (Hutchinson strain) in cultured human hepatoma cells *Proc. Natl. Acad. Sci. USA* 103:2310-2315.

Zhong, J., et al., 2005 Robust hepatitis C virus infection in vitro *Proc. Natl. Acad. Sci. USA* 102:9294-9299.

Zibert, A., et al., 1997 Early antibody response against hypervariable region 1 is associated with acute self-limiting infections of hepatitis C virus *Hepatology* 25:1245-1249.

\* cited by examiner

JFH1 HC-TN

4 Days after transfection

| Genomic region | nt position* | nt difference (%) | | | | aa position* | aa difference (%) | | | |
|---|---|---|---|---|---|---|---|---|---|---|
| | | H77C | HCV-1 | HC-J1 | HCV-UK | | H77C | HCV-1 | HC-J1 | HCV-UK |
| 5'UTR | 1-341 | 1 (0.3) | 0 (0.0) | 2 (0.6) | 2 (0.6) | | | | | |
| Core | 342-914 | 7 (1.2) | 13 (2.3) | 11 (1.9) | 15 (2.6) | 1-191 | 1 (0.5) | 3 (1.6) | 3 (1.6) | 3 (1.6) |
| E1 | 915-1490 | 24 (4.2) | 34 (5.9) | 43 (7.5) | 39 (6.8) | 192-383 | 6 (3.1) | 9 (4.7) | 11 (5.7) | 9 (4.7) |
| E2 | 1491-2579 | 70 (6.4) | 76 (7.0) | 81 (7.4) | 150 (13.8) | 384-746 | 25 (6.9) | 28 (7.7) | 28 (7.7) | 48 (13.2) |
| (HVR1) | 1491-1571 | 12 (14.8) | 13 (16.0) | 15 (18.5) | 32 (39.5) | 384-410 | 7 (25.9) | 9 (33.3) | 8 (29.6) | 15 (55.6) |
| p7 | 2580-2768 | 9 (4.8) | 10 (5.3) | 11 (5.8) | 22 (11.6) | 747-809 | 2 (3.2) | 3 (4.8) | 4 (6.3) | 5 (7.9) |
| NS2 | 2769-3419 | 36 (5.5) | 42 (6.5) | 47 (7.2) | 65 (10.0) | 810-1026 | 7 (3.2) | 8 (3.7) | 9 (4.1) | 18 (8.3) |
| NS3 | 3420-5312 | 86 (4.5) | 90 (4.8) | 109 (5.8) | 143 (7.6) | 1027-1657 | 12 (1.9) | 14 (2.2) | 16 (2.5) | 18 (2.9) |
| NS4A | 5313-5476 | 8 (4.8) | 9 (5.5) | 9 (5.5) | 17 (10.4) | 1658-1711 | 1 (1.9) | 1 (1.9) | 1 (1.9) | 3 (5.6) |
| NS4B | 5477-6257 | 32 (4.1) | 27 (3.5) | 44 (5.6) | 67 (8.6) | 1712-1972 | 6 (2.3) | 4 (1.5) | 9 (3.4) | 11 (4.2) |
| NS5A | 6258-7600 | 67 (5.0) | 74 (5.5) | 86 (6.4) | 108 (8.0) | 1973-2420 | 23 (5.1) | 21 (4.7) | 25 (5.6) | 30 (6.7) |
| NS5B | 7601-9374 | 53 (3.0) | 62 (3.5) | 73 (4.1) | 101 (5.7) | 2421-3011 | 5 (0.8) | 9 (1.5) | 8 (1.4) | 19 (3.2) |
| ORF | 342-9374 | 392 (4.3) | 437 (4.8) | 514 (5.7) | 727 (8.0) | 1-3011 | 88 (2.9) | 100 (3.3) | 114 (3.8) | 164 (5.4) |
| 3'UTR | 9375-9599 | | | | | | | | | |
| Variable region | 9375-9417 | 1 (2.3) | 0 (0.0) | 3 (7.0) | NA | | | | | |
| Conserved region | 9499-9599 | 0 (0.0) | NA | NA | NA | | | | | |

*The nucleotide and predicted amino acid positions correspond to those of pHC-TN.
NA: not available

Figure 5

Chimpanzee 1422*

| Week | Mutation rate (x10⁻³/site/year) | | Sd | Nd | ds/dn |
|---|---|---|---|---|---|
| | Nucleotide | Amino acid | | | |
| 19 | 23.63 | 17.27 | 61 | 17 | 11.1 |

Chimpanzee 1581†

| Week | Mutation rate (x10⁻³/site/year) | | Sd | Nd | ds/dn |
|---|---|---|---|---|---|
| | Nucleotide | Amino acid | | | |
| 8 | 0 | 0 | 0 | 0 | NA |
| 11 | 0 | 0 | 0 | 0 | NA |
| 14 | 11.51 | 23.03 | 2 | 4 | 1.52 |
| 18 | 14.39 | 34.53 | 2 | 8 | 0.76 |
| 27 | 6.40 | 11.51 | 3 | 7 | 1.30 |
| 32 | 3.45 | 6.91 | 1 | 2 | 1.52 |
| 36 | 24.47 | 25.91 | 11 | 6 | 5.58 |
| 45 | 3.38 | 9.59 | 1 | 5 | 0.61 |
| 52 | 4.11 | 9.87 | 1 | 4 | 0.76 |
| 52¶ | 3.65 | 6.64 | 13 | 20 | 1.98 |

Chimpanzee 1579†

| week | Mutation rate (x10⁻³/site/year) | | Sd | Nd | ds/dn |
|---|---|---|---|---|---|
| | Nucleotide | Amino acid | | | |
| 10 | 0 | 0 | 0 | 0 | NA |
| 13 | 0 | 0 | 0 | 0 | NA |
| 21 | 4.32 | 10.79 | 1 | 5 | 0.61 |
| 32 | 5.76 | 14.13 | 2 | 9 | 0.68 |
| 32¶ | 2.34 | 6.48 | 1 | 12 | 0.25 |

*Week 19 sequence was compared to HCV sequence obtained from acute phase plasma pool of chimpanzee 1422.
†At each time point the HC-TN sequence was compared with that obtained at the previous time point.
¶The HC-TN sequence obtained at week 52 from chimpanzee 1581 and week 32 from 1579 were also compared with that of inoculum.
NA: not applicable

| Week* | E2 401 | E2 433 | E2 461 | p7 767 | p7 793 | 834 | 837 | NS2 841 | NS2 861 | 1405 | NS3 1406 | 1583 | 1746 | NS4B 1747 | 1751 | 2064 | 2116 | 2118 | 2220 | NS5A 2223 | 2227 | 2278 | 2341 | 2358 | 2414 | NS5B 2664 | 3005 |
|---|---|---|---|---|---|---|---|---|---|---|---|---|---|---|---|---|---|---|---|---|---|---|---|---|---|---|---|
|  | S | L | P | S | M | Y | R | W | I | A | K | F | V | A | Q | A | V | S | D | D | I | S | P | S | K | D | I |
| 1 |  |  |  |  |  |  |  |  |  |  |  |  |  |  |  | T |  |  |  |  |  |  |  |  |  |  |  |
| 8 | S | L | P | S | M | Y | R | W | I | A | K | F | V | A | Q | T | V | S | D/g | D | I | S | P | S | K | D | — |
| 11 | S | L | P | S | M | Y | R | W | I | A | K | F | V | A | Q | T | V | S | D/G | D | — | S | P | S | K | D | — |
| 13 |  |  |  |  |  | Y/h | R/H | W/r | — |  |  |  |  |  |  |  |  | S | G/d | D | — | S |  |  |  |  |  |
| 14 | S | L | P | S | V | Y/h | R/H | W | — | A | K | F | V | A/t | H/q | A/t | V | S | G/d | D | — | S | P | S | K/E | D | — |
| 18 | S | L | P | S | V | Y | L | W | — | A | K | F | V | T/a | Q/h | T/a | V | S | D/g | D | — |  |  |  |  |  |  |
| 26 |  |  |  |  |  | Y/h | L | W | V/i |  |  |  |  |  |  |  | V | S | D | N |  |  |  |  |  |  |  |
| 27 | S | L | P | S | T | H/y | L | W | V/i | A | K | F | V | T | Q | T | V | P | D | N |  | P | P | S | E | G | — |
| 31 |  |  |  |  | T |  |  |  |  | T/a | K |  |  |  |  |  |  | P |  |  |  | P |  |  |  |  |  |
| 32 | S | L/F | S | S | T | H/Y | L | W/R | V | T | K | F | V | T | Q | T | V | P | D | D/n | — | P | P | S | E | G | — |
| 36 | S | F | S | S/p | T | Y | L | R | V | A | K | F | V | T | Q | T | V | P | D | D | — | P | P | S | E | G | — |
| 45 | G/s | F | S | P/s | T | Y | L | R | V | A/v/t/i | K/R | F | V/i | T | Q | T | V | P/S | D | D | V/i | P | P | S | E | G | T |
| 51 |  |  |  |  |  |  |  |  |  |  |  | L/f | I/v | T | Q | T | V/i | P | D | D | V | P | S/p | P/s | E | G | T |
| 52 | G | F | S | P | T | Y | L | R | V | A/t | R/k | L | V/i | T | Q | T/a | I/v | P | D | D | V | P | S/p | P | E | G | T |

Amino acid positions correspond to those of pHC-TN. Consensus sequence of viruses recovered from chimpanzee 1422 acute plasma pool is shown on top.
Dominant sequences recovered from the chimpanzee are shown in capital letter. Minor sequences recovered from the chimpanzee are shown in lower case letters.
Dominant amino acid changes are shaded. Note that two consecutive changes occurred at aa 793.
* The entire ORF sequence of HC-TN was determined at weeks 8, 11, 14, 18

| | E2 | p7 | NS2 | NS3 | | NS4A | NS5A | | | | | NS5B | |
|---|---|---|---|---|---|---|---|---|---|---|---|---|---|
| | 403 | 789 | 1018 | 1148 | 1563 | 1700 | 2252 | 2263 | 2341 | 2374 | 2414 | 2456 | 3008 |
| Week* | F | A | M | S | T | V | I | E | P | S | K | L | L |
| 10 | F | A | M | S | T | V | I | E | P | S | K | L | L |
| 13 | F | A | M | S | T | V | I | E | P | S | K | L | L |
| 20 | | | M | | | A/v | | | | | | | |
| 21 | F/l | | M/v | S | T | A/v | V/i | E/g | S | S/f | K/T/n | M/l | L/f |
| 31 | | T | | G | I/t | | | | | | | | |
| 32 | L | T | T | G | I/t | V | V | G | S | F | E | M | F |
| 33 | L | T | T/M | G | I/t | V | V | G | S | F | E | M | F |

Amino acid positions correspond to those of pHC-TN. Sequence of pHC-TN is shown on Top. Dominant sequences recovered from the chimpanzee are shown in capital letter. Minor sequences recovered from the chimpanzee are shown in lower case letters. Dominant amino acid changes are shaded.

* The entire ORF sequence of HC-TN was determined at weeks 10, 13, 21, 32 and 33. Only subdomains were analyzed at weeks 20 and 31.

Figure 8

CLONED GENOME OF INFECTIOUS HEPATITIS C VIRUS STRAIN HC-TN AND USES THEREOF

SEQUENCE LISTING

The present application is being filed along with a Sequence Listing in electronic format. The Sequence Listing is provided as a file entitled NIH367_001A_Sequence_Listing.TXT, created Apr. 2, 2008, which is 41 Kb in size. The information in the electronic format of the Sequence Listing is incorporated herein by reference in its entirety.

FIELD OF THE INVENTION

Aspects of the present invention relate to nucleic acid sequences, which comprise hepatitis C virus (HCV) sequences. In particular, some embodiments concern a nucleic acid sequence which comprises sequences of the infectious hepatitis C virus strain HC-TN. More embodiments relate to the use of the embodied nucleic acid sequences and polypeptides encoded by these nucleic acid sequences, and immunogens, vaccines, diagnostic assays, and methods to identify HCV antiviral agents.

BACKGROUND OF THE INVENTION

Hepatitis C virus (HCV) has a positive-sense single-strand RNA genome and is a member of the genus Hepacivirus within the Flaviviridae family of viruses (Rice, C. M. 1996 Flaviviridae: The viruses and their replication, In *Fields Virology* (B. N. Fields, D. M. Knipe, P. M. Howley, et al., Eds.), Third ed., pp. 931-959. Lippincott-Raven Publishers, Philadelphia). As for all positive-stranded RNA viruses, the genome of HCV functions as mRNA from which all viral proteins necessary for propagation are translated.

The viral genome of HCV is approximately 9600 nucleotides (nts) in length and consists of a highly conserved 5' untranslated region (UTR), a single long open reading frame (ORF) of approximately 9,000 nts and a complex 3' UTR. The 5' UTR contains an internal ribosomal entry site (Tsukiyama-Kohara, K. et al. 1992 *J. Virol.* 66:1476-1483; Honda, M., et al. 1996 *RNA* 2:955-968). The 3' UTR consists of a short variable region, a polypyrimidine tract of variable length and, at the 3' end, a highly conserved region of approximately 100 nucleotides (Kolykhalov, A. A. et al. 1996 *J. Virol.* 70:3363-3371; Tanaka, T et al. 1995 *Biochem. Biophys. Res. Commun.* 215:744-749; Tanaka, T. et al. 1996 *J. Virol.* 70:3307-3312; Yamada, N. et al. 1996 *Virology* 223:255-261). The last 46 nucleotides of this conserved region were predicted to form a stable stem-loop structure thought to be critical for viral replication (Blight, K. J. and Rice, C. M. 1997 *J. Virol.* 71:7345-7352; Ito, T. and Lai, M. M. C. 1997 *J. Virol.* 71:8698-8706; Tsuchihara, K. et al. 1997 *J. Virol.* 71:6720-6726). The ORF encodes a large polypeptide precursor that is cleaved into at least 10 proteins by host and viral proteinases (Rice, C. M. 1996 Flaviviridae: The viruses and their replication, In *Fields Virology* (B. N. Fields, D. M. Knipe, P. M. Howley, et al., Eds.), Third ed., pp. 931-959. Lippincott-Raven Publishers, Philadelphia). The predicted envelope proteins contain several conserved N-linked glycosylation sites and cysteine residues (Okamoto, H. et al. 1992 *Virology* 188:331-341). The NS3 gene encodes a serine protease and an RNA helicase and the NS5B gene encodes an RNA-dependent RNA polymerase.

A remarkable characteristic of HCV is its genetic heterogeneity, which is manifested throughout the genome (Bukh, J. et al. 1995 *Semin. Liver Dis.* 15:41-63). The most heterogeneous regions of the genome are found in the envelope genes, in particular the hypervariable region 1 (HVR1) at the N-terminus of E2 (Hijikata, M. et al. 1991 *Biochem. Biophys. Res. Commun.* 175:220-228; Weiner, A. J. et al. 1991 *Virology* 180:842-848). HCV circulates as a quasispecies of closely related genomes in an infected individual. Globally, six major HCV genotypes (genotypes 1-6) and multiple subtypes (a, b, c, etc.) have been identified (Bukh, J. et al. 1993 *PNAS USA* 90:8234-8238; Simmonds, P. et al. 1993 *J. Gen. Virol.* 74:2391-2399).

The nucleotide and deduced amino acid sequences among isolates within a quasispecies generally differ by <2%, whereas those between isolates of different genotypes vary by as much as 35%. Genotypes 1, 2 and 3 are found worldwide and constitute more than 90% of the HCV infections in North and South America, Europe, Russia, China, Japan and Australia (Foms, X. and Bukh, J. 1998 *Viral Hepatit. is Reviews* 4:1-19). Throughout these regions genotype 1 accounts for the majority of HCV infections but genotypes 2 and 3 each account for 5-15%.

At present, more than 80% of individuals infected with HCV become chronically infected and these chronically infected individuals have a relatively high risk of developing chronic hepatitis, liver cirrhosis and hepatocellular carcinoma (Hoofnagle, J. H. 1997 *Hepatology* 26:15S-20S). The current treatment for chronic hepatitis C involves administration of interferon (IFN) and ribavirin, which induces a sustained response in less than 50% of treated patients, and which has a poorer response in genotype 1 compared to genotypes 2 and 3 (Davis, G. L. et al. 1998 *N. Engl. J. Med.* 339:1493-1499; McHutchison, J. G. et al. 1998 *N. Engl. J. Med.* 339:1485-1492). Consequently, HCV is currently the most common cause of end stage liver failure and the reason for most liver transplants performed in the U.S. (Hoofnagle, J. H. 1997 *Hepatology* 26:15S-20S). As a result of the inability to develop a universally effective therapy against HCV infection, it is estimated that there are still more than 25,000 new infections yearly in the U.S. (Alter, M. J. 1997 *Hepatology* 26:62S-65S).

Despite the intense interest in the development of vaccines and therapies for HCV, progress has been hindered by the absence of a useful cell culture system and the lack of any small animal model for laboratory study. For example, while replication of HCV in several cell lines has been reported, such observations have turned out not to be highly reproducible. In addition, the chimpanzee is the only animal model, other than man, for this disease. Consequently, HCV has been studied only by using clinical materials obtained from patients or experimentally infected chimpanzees, an animal model whose availability is very limited.

Kolykhalov, A. A. et al. (1997 *Science* 277:570-574) and Yanagi et al. (1997 *PNAS USA* 94:8738-8743 and 1998 *Virology* 244:161-172) reported the derivation from HCV strains H77 (genotype 1a) and HC-J4 (genotype 1b) of cDNA clones of HCV that are infectious for chimpanzees. However, while these infectious clones will aid in studying HCV replication and pathogenesis and will provide an important tool for development of in vitro replication and propagation systems, it is important to have infectious clones of multiple strains and genotypes, given the extensive genetic heterogeneity of HCV and the potential impact of such heterogeneity on the development of effective therapies and vaccines for HCV. The need for more tools to better characterize HCV and the need for more HCV therapeutics and diagnostic approaches is manifest.

SUMMARY OF THE INVENTION

Aspects of the present invention relate to nucleic acid sequences, which comprise sequences of infectious hepatitis C virus of genotype 1a (HC-TN) and the polypeptides encoded by these nucleic acids. In some contexts, these nucleic acid sequences are referred to as "infectious nucleic acid sequence".

Nucleic acid sequences can include RNA, DNA, cDNA or any variant thereof-capable of directing host organism synthesis of a hepatitis C virus polypeptide. It is understood that nucleic acid sequence encompasses nucleic acid sequences, which due to degeneracy, encode the same polypeptide sequence as the nucleic acid sequences described herein. In some embodiments, the nucleic acids are codon-optimized for expression in a host (e.g., human or chimpanzee). Several programs and approaches to codon-optimize nucleic acids are known in the art.

Aspects of the invention include nucleic acids that comprise, consist, or consist essentially of a nucleic acid with SEQ ID NO: 1 or a fragment thereof, which encodes an antigenic peptide (e.g., fragments at least or equal to 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 130, 140, 150, 175, 200, 225, 250, 300, 350, 375, 400, 450, 500, 550, 600, 650, 700, 750, 800, 850, 900, 950, 1000, 1050, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500 or 9599 consecutive nucleotides of SEQ ID NO: 1 wherein said fragment encodes a peptide that is antigenic).

Some embodiments also include mutated forms of the nucleic acids described herein, including, but not limited to any one of the nucleic acids described herein comprising one or more point mutations, deletions or insertions. In some embodiments, a nucleic acid described herein can be deleted to determine the effect of the deleted gene or genes on the properties of the encoded virus such as its virulence and its ability to replicate. In an alternative embodiment, a mutation may be introduced into the infectious nucleic acid sequences to examine the effect of the mutation on the properties of the virus. Accordingly, some embodiments encompass methods or analyzing mutant nucleic acids for effects on viral phenotypes.

Desired embodiments include several HCV nucleic acid sequences with mutations that produce an attenuated hepatitis C virus. Preferred mutations that produce an attenuated phenotype are described herein. The nucleic acids, or the polypeptides encoded therefrom can be formulated into immunogenic compositions and for vaccines (e.g., DNA immunogens for delivery by electroporation, injection, powder injection).

Embodiments also include the use of the nucleic acid sequences described herein to produce attenuated viruses via passage in vitro or in vivo of the viruses produced by transfection of a host cell with the infectious nucleic acid sequence. Accordingly, attenuated viruses containing one or more of the nucleic acids described herein are embodiments.

More embodiments concern the use of the nucleic acid sequences described herein, to produce a polypeptide. The nucleic acids suitable for polypeptide production include a nucleic acid sequence as described herein, mutant or modified infectious nucleic acid sequences as described herein, chimeric nucleic acid sequences and sequences which comprise the genome of attenuated viruses produced from a nucleic acid sequence described herein. In some embodiments, said polypeptides are fully or partially purified from cells, which have been transfected with a nucleic acid sequence described herein.

In some embodiments, the polypeptides are produced recombinantly from a full-length or fragment of a nucleic acid sequence described herein, for example the nucleic acid sequence of SEQ ID NO: 1 or fragments thereof (e.g., fragments at least or equal to 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 130, 140, 150, 175, 200, 225, 250, 300, 350, 375, 400, 450, 500, 550, 600, 650, 700, 750, 800, 850, 900, 950, 1000, 1050, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500 or 9599 consecutive nucleotides of SEQ ID NO: 1 wherein said fragment encodes a peptide that is antigenic). In yet another embodiment, the polypeptides encoded by the nucleic acids described herein are chemically synthesized.

The polypeptides can be used as immunogens and can be used in diagnostic assays to detect the presence of HCV in biological samples. The polypeptides can also be used to screen anti-HCV compounds (e.g., protease inhibitors).

Accordingly, aspects of the invention relate to methods of inoculating or immunizing mammals, especially humans against hepatitis C, wherein one or more of the nucleic acids or polypeptides provided to a subject (e.g., a human) that has been identified as one in need of an immune response to HCV. Optimally, said subject can be measured for the immune response to HCV before, during, or after inoculation with an immunogen as described herein. In more embodiments, a vaccine or immunogenic composition comprises one or more polypeptides made from a nucleic acid sequence of described herein. In another embodiment; the vaccine or immunogenic composition comprises a hepatitis C virus produced by transfection of host cells with the nucleic acid sequences of the invention.

In other embodiments, a method of inducing an immune response to HCV comprises administering to a mammal a polypeptide encoded by a nucleic acid sequence described herein in an amount effective to induce an immune response to hepatitis C. In another embodiment, the method comprises administering to a mammal a hepatitis C virus prepared as described herein in an amount effective to induce an immune response against hepatitis C. In yet another embodiment, the method comprises administering to a mammal a nucleic acid sequence as described herein in an amount effective to induce protective immunity against hepatitis C (e.g., by electroporation, injection, transdermal route). Aspects of the invention also relate to hepatitis C viruses produced by host cells transfected with a nucleic acid sequence as described herein.

Accordingly, pharmaceutical compositions comprising a nucleic acid sequence as described herein and/or a hepatitis C viruses encoded by said nucleic acids are embodiments. Aspects of the invention further provide pharmaceutical compositions comprising polypeptides encoded by a nucleic acid sequence described herein or fragments thereof. The pharmaceutical compositions may be used prophylactically or therapeutically. In particular, said nucleic acids can be given to subjects (e.g., humans) identified as those in need of an immune response using HCV.

Some embodiments also relate to antibodies to the hepatitis C virus or its encoded polypeptides as described herein and to pharmaceutical compositions comprising these antibodies. Aspects of the invention also relate to the use of the nucleic acid sequences of the invention to identify cell lines capable of supporting the replication of HCV in vitro. More embodiments concern the use of the nucleic acid sequences of the invention or their encoded viral enzymes (e.g. NS3 serine protease, NS3 helicase, NS5B RNA polymerase) to develop screening assays to identify antiviral agents for HCV.

Further embodiments provided herein include a purified or isolated nucleic acid molecule which encodes human hepatitis C virus of genotype 1a and strain HC-TN or sequence complementary thereto, the molecule capable of expressing the virus when transfected into cells. In certain aspects, the molecule encodes the amino acid sequence of SEQ ID NO: 2. In certain aspects, the molecule comprises the nucleic acid sequence of SEQ ID NO: 1. Other aspects include vectors that comprise the nucleic acid molecules described above, and host cells that comprise the vectors.

Also provided herein is an isolated or purified polypeptide comprising the amino acid sequence of SEQ ID NO: 2 or an antigenic fragment thereof comprising at least 9 consecutive amino acids. In certain aspects, the polypeptide comprises the amino acid sequence of SEQ ID NO: 2. In certain aspects, the polypeptide is a fragment of SEQ ID NO: 2 at least 100 at least 300 consecutive amino acids in length.

Other embodiments include a method for producing a hepatitis C virus comprising transfecting a host cell with a nucleic acid described herein.

Other embodiments include a method for assaying candidate antiviral agents for activity against HCV, comprising: (a) exposing a cell comprising a nucleic acid that encodes SEQ ID NO: 2 or a fragment thereof to a candidate antiviral agent; and (b) measuring the presence or absence of hepatitis C virus replication or NS3 protease activity in the cell of step (a). In certain aspects, the replication activity in step (b) is measured by at least one of the following: negative strand RT-PCR, quantitative RT-PCR, Western blot, immunofluorescence, or infectivity in a susceptible animal.

Also provided herein is a method for assaying candidate antiviral agents for activity against HCV, comprising: (a) exposing a cell comprising a nucleic acid that encodes SEQ ID NO: 2 or a fragment thereof to a candidate antiviral agent; and (b) measuring the presence or absence of hepatitis C virus helicase or polymerase activity in the cell of step (a).

Other embodiments include a method for assaying candidate antiviral agents for activity against HCV, comprising: a) exposing an HCV protease encoded by a nucleic acid sequence as described herein or a fragment thereof that contains protease activity to a candidate antiviral agent in the presence of a protease substrate; and b) measuring the protease activity of the protease. In certain aspects, the HCV protease is selected from the group consisting of an NS3 domain protease, an NS3-NS4A fusion polypeptide, or an NS2-NS3 protease.

Also provided herein is a method of inducing an immune response to HCV comprising: identifying an animal in need of an immune response to HCV; and providing to the animal a composition that comprises the polypeptide encoded by the nucleic acid of SEQ ID NO: 1 or a nucleic acid that encodes a polypeptide comprising the sequence of SEQ ID NO: 2. In certain aspects the method further comprises measuring the immune response to the polypeptide encoded by SEQ ID NO: 1 or a fragment thereof.

Representing the evolution of HC-TN, the HC-TN genome is shown as a vertical bar with the core (C) at the top and NS5B at the bottom. Solid black lines with capital letters indicate new amino acid changes that were identified when a sequence was compared with the sequence obtained at the previous time point. Underlined capital letters indicate mutations that had occurred by one time point but had changed back to the original sequence by the next time point analyzed. Solid black lines without capital letters represent amino acid changes that persisted. The week the sequence was analyzed is indicated at the bottom of each genome. For neutralizing antibodies, the percent neutralization of retroviral pseudovirus particles bearing the HCV envelope proteins (>50% was considered significant) is shown. The peripheral and intrahepatic CD4+ T-cell responses to core (red), NS3 (orange), NS3-NS4 (green), and NS5 (blue) are shown as specific SI. A specific SI of >2 was considered significant. At weeks tested in which the SI was ≦2 against all four antigens, the negative result is indicated by a black bar (with a value of 2). The intrahepatic CD8+ T-cell response is represented as the percentage of intrahepatic CD8+ T cells that produced gamma interferon (IFN-γ) after stimulation with transiently expressed HCV proteins. vv 1-1488 denotes vaccinia virus vHCV(1-1488); vv 827-3011 denotes vaccinia virus vHCV (827-3011).

Figures 1, 3A:
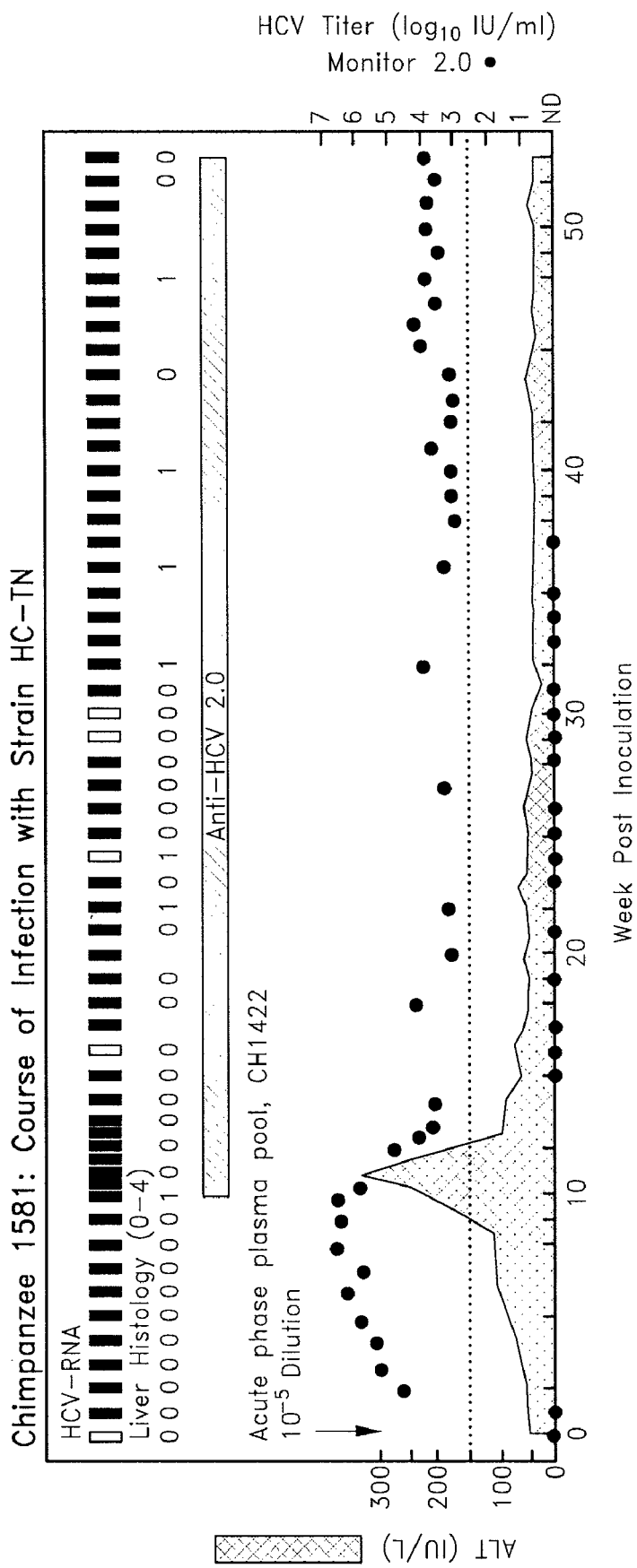
Figure 3A:
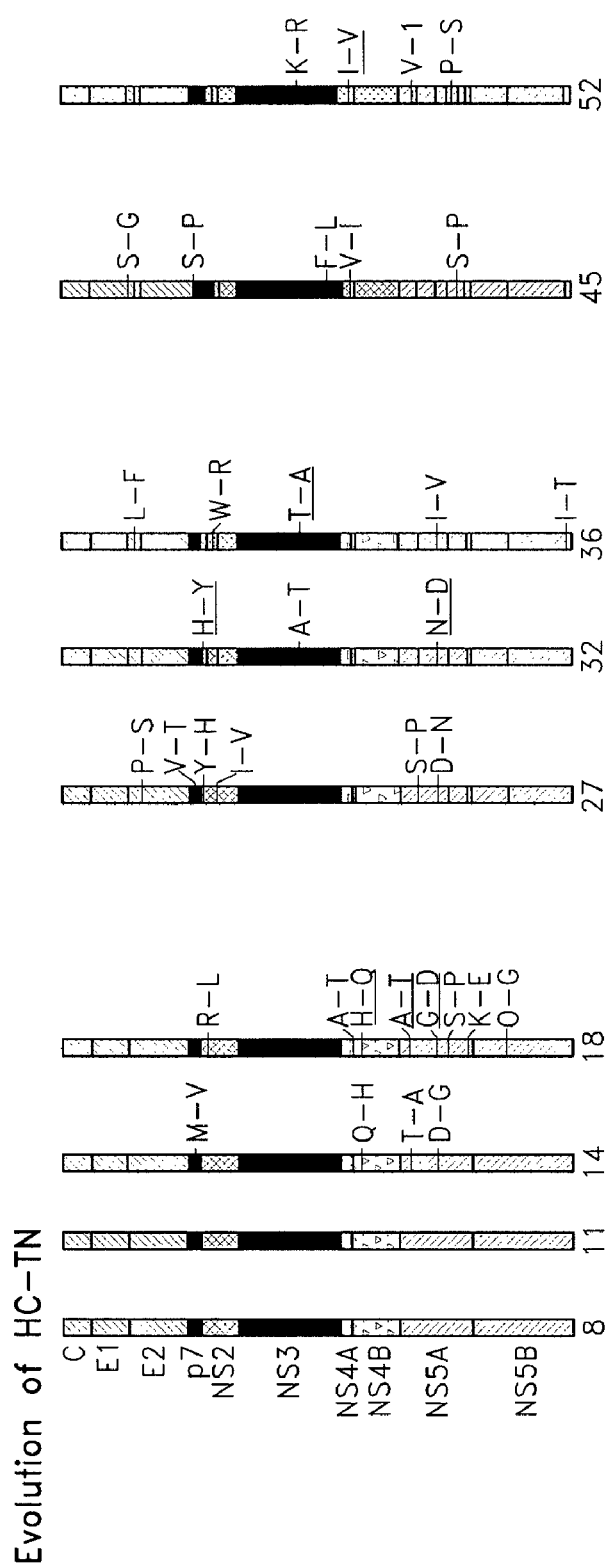
FIG. 3 shows the course of infection, viral evolution, and immune responses in (A) CH1581 and (B) CH1579, which were infected with HCV strain HC-TN (quasipolyclonal and monoclonal infections, respectively) as described in the description for FIG. 1.
Figure 2:
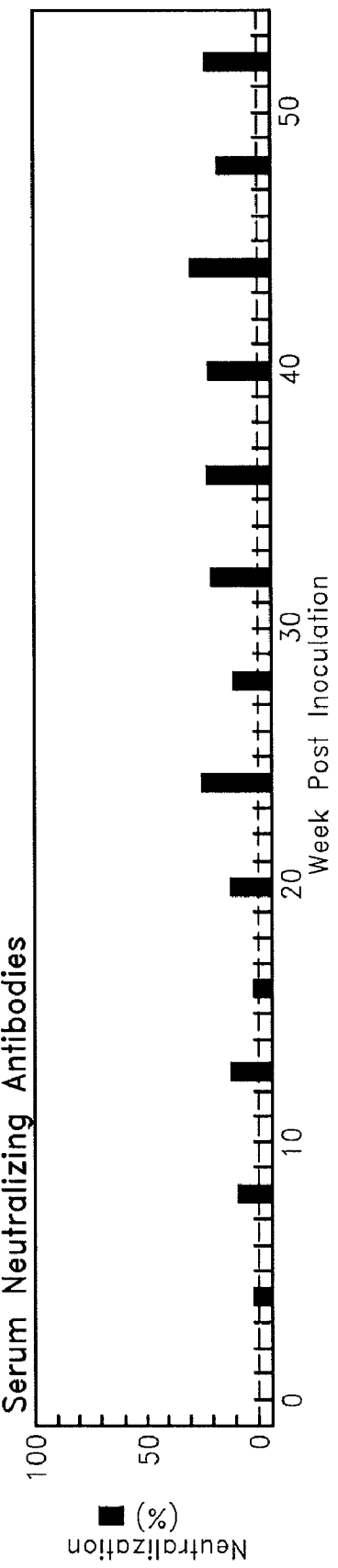
Figures 3, 3A:
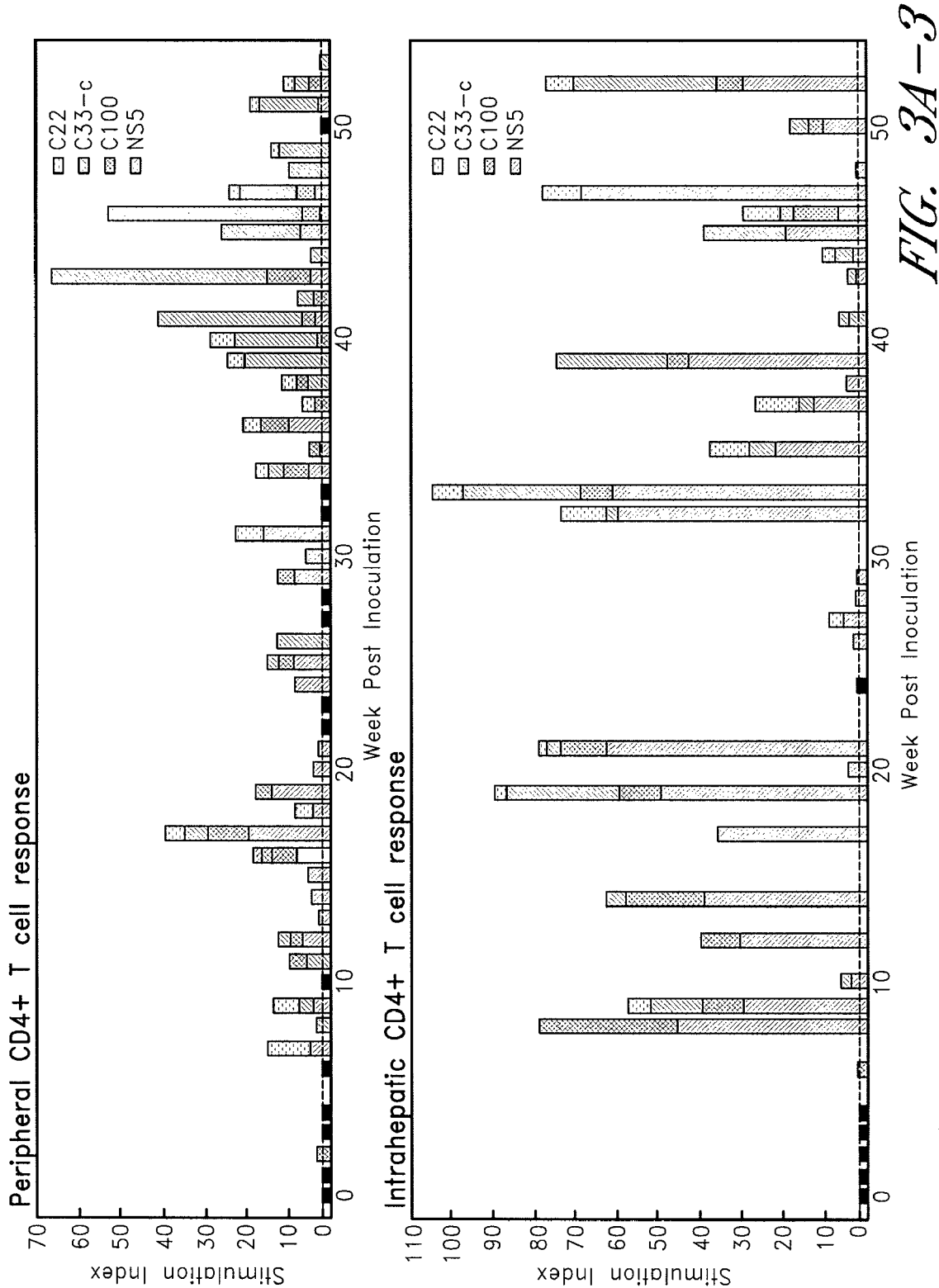
Figures 3, 3A, 4:
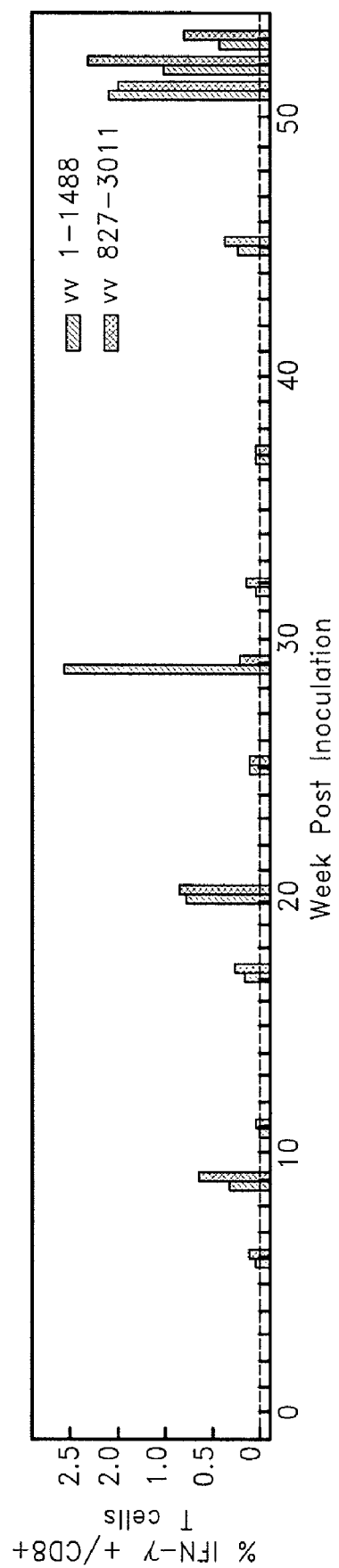

FIG. 4 shows testing for replication of pHC-TN in vitro. Huh7.5 cells were transfected with RNA transcripts of pJFH1 and pHC-TN. Immunofluorescence staining was performed with an HCV core-specific mouse monoclonal antibody.

FIG. 5 is a table showing differences in nucleotide and predicted amino acid sequences between HC-TN and other genotype 1a strains.

FIG. 6 is a table showing nucleotide and amino acid substitutions observed in chimpanzees infected with HC-TN.

FIG. 7 is a table showing evolution of HC-TN polyprotein in CH1581.

FIG. 8 is a table showing evolution of HC-TN polyprotein in CH1579.

DETAILED DESCRIPTION OF THE PREFERRED EMBODIMENT

Acute hepatitis C is often asymptomatic. However, the disease burden of hepatitis C virus (HCV) is very significant, since about 170 million people worldwide are chronically infected, leading to chronic hepatitis, liver cirrhosis, and hepatocellular carcinoma in a significant proportion of infected individuals. HCV is now the leading cause of liver transplantation (Seeff, L. B. et al. 2001 *Hepatology* 33:455-463). The chimpanzee is the only animal model in which to study the natural history of HCV (Bukh, J. 2004 *Hepatology* 39:1469-1475). Experimental infections permit collection of frequent samples, including liver tissue samples, before infection and during the acute phase and thus permit studies of early virological and immunological events that define the outcome. Furthermore, by inoculating chimpanzees intrahepatically with RNA transcripts of infectious HCV clones it is possible to study monoclonal virus infections (Kolykhalov, A. A. et al. 1997 *Science* 277:570-574; Yanagi, M. et al. 1999 *Virology* 262:250-263; Yanagi, M. et al. 1997 *Proc. Natl. Acad. Sci. USA* 94:8738-8743; Yanagi, M. et al. 1998 *Virology* 244:161-172), in which virus interaction with the host is not initially influenced by a viral quasispecies. Also, in the study of the association between HCV and pathogenesis, infection from a molecular clone eliminates the possibility that an observed phenotype is caused by a coinfecting agent.

Fulminant hepatitis caused by hepatotropic viruses is a rare but potentially fatal condition. Initially, HCV was not recognized as an etiological agent of fulminant hepatitis (Wright, T. L. et al. 1991 *Ann. Intern. Med.* 115:111-112). However, a significant number of Japanese patients with fulminant hepatitis had evidence of HCV infection (Muto, Y. et al. 1990 *Gastroenterol. Jpn.* 25:32-35, Yanagi, M. et al. 1991 *N. Engl. J. Med.* 324:1895-1896). Subsequently, the temporal relationship between transfusion-acquired HCV (genotype 1b) infection and development of fulminant hepatitis was described (Farci, P. et al. 1996 *N. Engl. J. Med.* 335:631-634). Certain HCV strains, including strain HC-TN, recovered from a patient with fulminant hepatitis, appear to be associated with the development of severe hepatitis (Farci, P. et al. 1999 *J. Infect. Dis.* 179:1007-1011, Kato, T. et al. 2001 *J. Med. Virol.* 64:334-339). To study the relationship between HC-TN and disease phenotype, this strain was transmitted to chimpanzees and an infectious clone was constructed to investigate monoclonal infection in a transfected chimpanzee.

The host and viral factors that determine the outcome of primary HCV infection are poorly understood. The host resolves less than 30% of infections. Viral clearance is associated with vigorous cellular immune responses (Cooper, S. et al. 1999 *Immunity* 10:439-449; Lechner, F. et al. 2000 *J. Exp. Med.* 191:1499-1512; Thimme, R. et al. 2001 *J. Exp. Med.* 194:1395-1406), but persistence may be associated with viral escape from such T-cell responses (Erickson, A. L. et al. 2001 *Immunity* 15:883-895).

Chimpanzees have been used to study the virological and immunological correlates of disease and outcome of acute HCV infection (Forns, X. et al. 2000 *Proc. Natl. Acad. Sci. USA* 97:13318-13323; Su, A. I. et al. 2002 *Proc. Natl. Acad. Sci. USA* 99:15669-15674, Thimme, R. et al. 2002 *Proc. Natl. Acad. Sci. USA* 99:15661-15668). Animals with viral clearance or with transient clearance followed by persistence at low titers had significant intrahepatic CD4[+] and CD8[+] T-cell responses, as well as an induction of gamma interferon and gamma interferon-induced genes in the liver. Thus, the initial control of HCV is mediated by intrahepatic cellular immune responses. However, it is still unclear why animals with significant intrahepatic responses may have different outcomes.

Nucleic Acids, Mutants and Deletions

Some embodiments described herein concern a nucleic acid sequence, which comprises a nucleic acid that encodes infectious hepatitis C virus of strain HC-TN, genotype 1a. Embodiments include, for example, the nucleic acid sequence of SEQ ID NO: 1 and fragments thereof (e.g., fragments at least or equal to 30, 33, 36, 39, 42, 45, 48, 51, 54, 57, 60, 63, 66, 69, 72, 75, 78, 81, 84, 87, 90, 93, 96, 99, 102, 105, 108, 111, 114, 117, 120, 130, 140, 150, 175, 200, 225, 250, 300, 350, 375, 400, 450, 500, 550, 600, 650, 700, 750, 800, 850, 900, 950, 1000, 1050, 1100, 1200, 1300, 1400, 1500, 1600, 1700, 1800, 1900, 2000, 2500, 3000, 3500, 4000, 4500, 5000, 5500, 6000, 6500, 7000, 7500, 8000, 8500, 9000, 9500 or 9599 consecutive nucleotides of SEQ ID NO: 1 wherein said fragment encodes a peptide that is antigenic). The nucleic acid sequence of SEQ ID NO: 1 is contained in a plasmid construct deposited with the American Type Culture Collection (ATCC) on Apr. 2, 2008 and having ATCC accession number PTA-9127.

Embodiments also include mutants or modifications of the nucleic acid sequences described herein. The term "mutations" may in some contexts refer to point mutations, deletions and insertions. Such mutations can be produced by techniques known to those of skill in the art such as site-directed mutagenesis, fusion PCR, and restriction digestion followed by re-ligation.

One may delete all or part of a gene described herein or part of the 5' or 3' nontranslated region contained in an infectious nucleic acid sequence and then transfect a host cell (animal or cell culture) with the mutated sequence and measure viral replication in the host by methods known in the art such as RT-PCR. Preferred genes include, but are not limited to, the P7, NS3, NS4A, NS4B and NS5A genes. Of course, those of ordinary skill in the art will understand that deletion of part of a gene, preferably the central portion of the gene, may be preferable to deletion of the entire gene in order to conserve the cleavage site boundaries which exist between proteins in the HCV polyprotein and which may be necessary for proper processing of the polyprotein.

In the alternative, if the transfection is into a host animal such as a chimpanzee, one can monitor the virulence phenotype of the virus produced by transfection of the mutated infectious nucleic acid sequence by methods known in the art such as measurement of liver enzyme levels (alanine aminotransferase (ALT) or isocitrate dehydrogenase (ICD)) or by histopathology of liver biopsies. Thus, mutations of the infectious nucleic acid sequences may be useful in the production of attenuated HCV strains suitable for use as an immunogenic composition or a vaccine.

Production of HCV Virus and Immunogens

Embodiments also include the use of a nucleic acid described herein to produce attenuated viral strains via passage in vitro or in vivo of the virus produced by transfection with the infectious nucleic acid sequence. Accordingly, methods of producing attenuated viral strains include subjecting virulent HCV virus to a very large number of successive serial passages in cell cultures. For example, attenuated non-pathogenic, immunogenically active HCV virus strain is obtained by subjecting virulent virus to greater than 50, 100, 150, 200, 250, 300 or 350 serial passages in cell cultures.

Embodiments also include the use of the nucleic acid sequence described herein to identify cell lines capable of supporting the replication of HCV. In such embodiments, a candidate cell line is transfected with the nucleic acid using known methods. Transfected candidate cells are incubated under cell culture conditions conducive for viral replication. Replication of the encoded virus is detected by known methods, such as immunofluorescence staining with anti-HCV antibodies, Western blot detection or methods to detect RNA transcription.

In particular, it is contemplated that the mutations of the infectious nucleic acid sequence described herein and the production of chimeric sequences as discussed above may be useful in identifying sequences critical for cell culture adaptation of HCV and hence, may be useful in identifying cell lines capable of supporting HCV replication.

Transfection of tissue culture cells with the nucleic acid sequences described herein may be done by methods of transfection known in the art such as electroporation, precipitation with DEAE-Dextran or calcium phosphate or liposomes.

In some embodiments, the method comprises the growing of animal cells, especially human cells, in vitro and transfecting the cells with a nucleic acid as described herein, and determining if the cells show indicia of HCV infection. Such indicia include the detection of viral antigens in the cell, for example, by immunofluorescence procedures well known in the art; the detection of viral polypeptides by Western blotting using antibodies specific therefore; and the detection of newly transcribed viral RNA within the cells via methods such as RT-PCR. The presence of live, infectious virus particles following such tests may also be shown by injection of cell culture medium or cell lysates into healthy, susceptible animals, with subsequent exhibition of the signs and symptoms of HCV infection.

Suitable cells or cell lines for culturing HCV include, but are not limited to, lymphocyte and hepatocyte cell lines known in the art.

Alternatively, primary hepatocytes can be cultured, and then infected with HCV; or, the hepatocyte cultures could be derived from the livers of infected chimpanzees. In addition, various immortalization methods known to those of ordinary skill in the art can be used to obtain cell lines derived from hepatocyte cultures. For example, primary hepatocyte cultures may be fused to a variety of cells to maintain stability.

Embodiments also include the in vitro and in vivo production of hepatitis C viruses from the nucleic acid sequences described herein. In some embodiments, the nucleic acids described herein are inserted into an expression vector that is operative in eukaryotic cells. Eukaryotic expression vectors suitable for high efficiency gene expression in vivo are well known, and include, but are not limited to, plasmids, vaccinia viruses, retroviruses, adenoviruses and adeno-associated viruses. Accordingly, plasmids that comprise the nucleic acids described herein are embodiments of the invention.

In more embodiments, the sequences contained in the recombinant expression vector are transcribed in vitro to produce RNA transcripts, which encode a hepatitis C virus as described herein. The hepatitis C virus may then be produced by transfecting suitable host cells with either the in vitro transcription mixture containing the RNA transcripts or with a recombinant expression vector containing a nucleic acid sequence described herein.

The hepatitis C viruses produced from the sequences described herein may be purified or partially purified from the transfected cells. In a preferred embodiment, the viruses are partially purified prior to formulation into immunogens, a pharmaceutical composition and/or a vaccine.

Embodiments therefore include hepatitis C viruses produced from the nucleic acid sequences described herein, and uses as immunogens which can be live or killed (e.g., formalin inactivated) vaccine or immunogenic compositions that can be used to prevent hepatitis C in a mammal or to induce an immune response to an HCV antigen. For example, attenuated, live strains of attenuated HCV as described herein are purified from cell culture supernates and provided to a mammal. Alternatively, viruses are purified from cell culture supernates and inactivated by treatment with an appropriate chemical agent such as formalin which preserves their antigenicity and immunogenicity while destroying their infectivity. The live or inactivated virus can be mixed with a suitable adjuvant and used to immunize mammals in order to elicit high titers of virus neutralizing antibodies and protect the immunized mammal from disease caused by HCV.

In an alternative embodiment, the immunogen described herein may be an infectious nucleic acid sequence, a chimeric nucleic acid sequence, or a mutated infectious nucleic acid sequence, which encodes a hepatitis C virus. Where the sequence is a cDNA sequence, the cDNAs and their RNA transcripts may be used to transfect a mammal by direct injection into the liver tissue of the mammal as described in the Examples. For example, SEQ ID NO: 1 or fragments thereof may be used as an immunogen.

Alternatively, direct gene transfer may be accomplished via administration of a eukaryotic expression vector containing a nucleic acid sequence as described herein. Where the immunogen or antigen is to be DNA (e.g., preparation of a DNA vaccine composition), suitable promoters include Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine and human metalothionein can be used. Examples of polyadenylation signals useful with some embodiments, especially in the production of a genetic vaccine for humans, include but are not limited to, SV40 polyadenylation signals and LTR polyadenylation signals. In particular, the SV40 polyadenylation signal, which is in pCEP4 plasmid (INVITROGEN®, San Diego Calif.), referred to as the SV40 polyadenylation signal, is used.

Delivery of said DNA vaccines, preferably codon-optimized DNA vaccines or optimized expression in a suitable host (e.g., human, horse, dog, cat, pig, chicken or rodent), can be accomplished using a variety of methods (e.g., MEDPULSAR® electroporation therapy system, microneedle injection devices, and ballistic gene transfer devices, such as powder injection devices), which are commercially available. Constructs comprising a codon-optimized nucleic acid described herein, or fragments thereof can be provided for any one or more of the uses described herein because the host animal can produce the protein from the nucleic acid. Accordingly, treatments such as nucleic acid-based vaccine therapeutics can be accomplished by delivering a construct comprising one or more of the nucleic acids described herein.

The nucleotide sequences encoding the full-length hepatitis C virus, or fragments thereof can be modified to generate sequences optimized for expression in human cells without altering the encoded polypeptide sequences. Computer algorithms are available for codon optimization. For example, web-based algorithms (e.g., Sharp et al. (1988) Nucleic Acids Res. 16:8207-11, hereby incorporated by reference) can be used to generate a nucleotide sequence with optimized expression in a suitable host (e.g., human, horse, dog, cat, pig, chicken or rodent).

In yet another embodiment, the immunogen may be a polypeptide encoded by the nucleic acid sequences described herein. Embodiments therefore also relate to polypeptides produced from the nucleic acid sequences described herein or fragments thereof. That is, some embodiments include the polynucleotides of SEQ ID NO: 2 or also immunogenic fragments thereof (e.g., immunogenic or antigenic fragment at least or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 115, 120, 150, 130, 135, 140, 145, 150, 155, 160, 165, 170, 175, 180, 185, 190, 195, 200, 225, 250, 275, 300, 350, 375, 400, 425, 450, 475, 500, 525, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000 or 3011 amino acids in length). In some embodiments, the polypeptides are recombinantly produced from the nucleic acid sequences described herein or isolated fragments thereof, or said nucleic acids can be purified, or partially purified, from transfected cells using available methods. In an alternative embodiment, the polypeptides may be purified or partially purified from viral particles produced via transfection of a host cell with the nucleic acid sequences described herein. Such polypeptides might, for example, include either capsid or envelope polypeptides prepared from the sequences of the present invention.

Pharmaceutical Preparations and Methods of Administration

When used as immunogens, the nucleic acid sequences described herein, or the polypeptides or viruses produced therefrom, are preferably partially purified prior to formulation of the immunogens or pharmaceutical composition or vaccine.

When used as an immunogen or vaccine, the sequences and the polypeptide and virus products thereof, can be administered or provided alone or in a suitable diluent, including, but not limited to, water, saline, oil or a buffered solution. The immunogen, vaccine, polypeptide or nucleic acids as described herein may be administered or provided to an animal, especially a mammal, and most especially a human, by a variety of routes, including, but not limited to, intradermally, intramuscularly, subcutaneously, transdermally, or in any combination thereof.

The amount of immunogen, vaccine, polypeptide or nucleic acid to provide for prophylactic or therapeutic purposes will vary depending on the route selected and the immunogen (nucleic acid, virus, polypeptide) administered. The amounts suitable for prophylactic treatment can be experimentally determined and may vary on the patient population identified to receive the immunogen, vaccine, polypeptide or nucleic acid.

The compositions described herein may be administered or provided once or periodically until a suitable titer of anti-HCV antibodies or HCV-specific T cells appear. For nucleic acid immunogens, a suitable amount of nucleic acid sequence to be used for prophylactic purposes may include a range of from about 100 μg to about 5 mg and most preferably in the range of from about 500 μg to about 2 mg. For a polypeptide, a suitable amount to use for prophylactic purposes is preferably 100 ng to 100 μg and for a virus $10^2$ to $10^6$ infectious doses.

A vaccine or immunogen as described herein may be employed in such forms as capsules, liquid solutions, suspensions or elixirs for oral administration, or sterile liquid forms such as solutions or suspensions. An inert carrier is preferably used, such as saline or phosphate-buffered saline, or any such carrier in which the HCV polypeptide or nucleic acid as described herein can be suitably suspended. The vaccines or immunogens may be in the form of single dose preparations or in multi-dose flasks, which can be utilized for mass-vaccination programs of both animals and humans. For purposes of using the vaccines described herein, reference is made to Remington's Pharmaceutical Sciences, Mack Publishing Co., Easton, Pa., Osol (Ed.) (1980); and New Trends and Developments in Vaccines, Voller et al. (Eds.), University Park Press, Baltimore, Md. (1978), both of which provide much useful information for preparing and using vaccines. Of course, the polypeptides described herein, when used as vaccines or immunogens, can include, as part of the composition or emulsion, a suitable adjuvant, such as alum (or aluminum hydroxide) when humans are to be vaccinated, to further stimulate production of antibodies by immune cells. When nucleic acids, viruses or polypeptides are used for vaccination purposes, other specific adjuvants such as CpG motifs (Krieg, A. K. et al. (1995) and (1996)), may prove useful.

When the nucleic acids, viruses and polypeptides described herein are used as vaccines or inocula, they will normally exist as physically discrete units suitable as a unitary dosage for animals, especially mammals, and most especially humans, wherein each unit will contain a predetermined quantity of active material calculated to produce the desired immunogenic effect in association with the required diluent. The dose of said vaccine or inoculum according to the present invention is administered at least once. In order to increase the antibody level, a second or booster dose may be administered at some time after the initial dose. The need for, and timing of, such booster dose will, of course, be determined within the sound judgment of the administrator of such vaccine or inoculum and according to sound principles well known in the art. For example, such booster dose could reasonably be expected to be advantageous at some time between about 2 weeks to about 6 months following the initial vaccination. Subsequent doses may be administered as indicated.

The nucleic acid sequences, viruses and polypeptides described herein can also be administered or provided for purposes of therapy, where a mammal, especially a primate, and most especially a human, is already infected, as shown by well known diagnostic measures. When the nucleic acid sequences, viruses or polypeptides of the present invention are used for such therapeutic purposes, much of the same criteria will apply as when it is used as a vaccine, except that inoculation will occur post-infection. Thus, when the nucleic acid sequences, viruses or polypeptides of the present invention are used as therapeutic agents in the treatment of infection, the therapeutic agent comprises a pharmaceutical composition containing a sufficient amount of said nucleic acid sequences, viruses or polypeptides so as to elicit a therapeutically effective response in the organism to be treated. Of course, the amount of pharmaceutical composition to be administered or provided will, as for vaccines, vary depending on the immunogen contained therein (nucleic acid, polypeptide, virus) and on the route of administration.

The therapeutic agent as described herein can thus be administered by subcutaneous, intramuscular or intradermal routes. One skilled in the art will certainly appreciate that the amounts to be administered for any particular treatment protocol can be readily determined without undue experimentation. Of course, the actual amounts will vary depending on the route of administration as well as the sex, age, and clinical status of the subject which, in the case of human patients, is to be determined with the sound judgment of the clinician.

The therapeutic agent described herein can be employed in such forms as capsules, liquid solutions, suspensions or elixirs, or sterile liquid forms such as solutions or suspensions. An inert carrier is preferably used, such as saline, phosphate-buffered saline, or any such carrier in which the HCV of the present invention can be suitably suspended. The therapeutic agents may be in the form of single dose preparations or in the multi-dose flasks which can be utilized for mass-treatment programs of both animals and humans. Of course, when the nucleic acid sequences, viruses or polypeptides of the present invention are used as therapeutic agents they may be administered as a single dose or as a series of doses, depending on the situation as determined by the person conducting the treatment.

Antibodies

The nucleic acids, polypeptides and viruses described herein can also be utilized in the production of antibodies against HCV. The term "antibody" is herein used to refer to immunoglobulin molecules and immunologically active portions of immunoglobulin molecules. Examples of antibody molecules are intact immunoglobulin molecules, substantially intact immunoglobulin molecules and portions of an immunoglobulin molecule, including those portions known in the art as Fab, F(ab')2 and F(v) as well as chimeric antibody molecules.

Thus, the polypeptides, viruses and nucleic acid sequences described herein can also be used in the generation of antibodies that immunoreact (i.e., specific binding between an antigenic determinant-containing molecule and a molecule containing an antibody combining site such as a whole antibody molecule or an active portion thereof) with antigenic determinants on the surface of hepatitis C virus particles.

Aspects of the present invention therefore also relate to antibodies produced following immunization with the nucleic acid sequences, viruses or polypeptides of the present invention. These antibodies are typically produced by immunizing a mammal with an immunogen or vaccine to induce antibody molecules having immunospecificity for polypeptides or viruses produced in response to infection with the nucleic acid sequences of the present invention. When used in generating such antibodies, the nucleic acid sequences, viruses, or polypeptides described herein may be linked to some type of carrier molecule. The resulting antibody molecules are then collected from said mammal.

The antibody molecules described herein may be polyclonal or monoclonal. Monoclonal antibodies are readily produced by methods well known in the art. Portions of immunoglobin molecules, such as Fabs, as well as chimeric antibodies, may also be produced by methods well known to those of ordinary skill in the art of generating such antibodies.

The antibodies described herein may also be contained in blood, plasma, serum, hybridoma supernatants, and the like. Alternatively, the antibody of the present invention is isolated to the extent desired by well known techniques such as, for example, using DEAE Sephadex. The antibodies produced as described herein may be further purified so as to obtain specific classes or subclasses of antibody such as IgM, IgG, IgA, and the like. Antibodies of the IgG class are preferred for purposes of passive protection. The antibodies of the present invention are useful in the prevention and treatment of diseases caused by hepatitis C virus in animals, especially mammals, and most especially humans. In providing the antibodies of the present invention to a recipient mammal, preferably a human, the dosage of administered antibodies will vary depending on such factors as the mammal's age, weight, height, sex, general medical condition, previous medical history, and the like. In general, recipient mammal is given a dosage of antibodies in the range of from about 1 mg/kg body weight to about 10 mg/kg body weight of the mammal, although a lower or higher dose may be administered if found desirable.

Such antibodies will normally be administered by intravenous or intramuscular route as an inoculum. The antibodies described herein are intended to be provided to the recipient subject in an amount sufficient to prevent, lessen or attenuate the severity, extent or duration of any existing infection.

The antibodies prepared by use of the nucleic acid sequences, viruses or polypeptides described herein are also highly useful for diagnostic purposes. For example, the antibodies can be used as in vitro diagnostic agents to test for the presence of HCV in biological samples taken from animals, especially humans. Such assays include, but are not limited to, radioimmunoassays, EIA, fluorescence, Western blot analysis and ELISAs. In one such embodiment, the biological sample is contacted with antibodies described herein and a labeled second antibody is used to detect the presence of HCV to which the antibodies are bound.

Such assays may be, for example, direct where the labeled first antibody is immunoreactive with the antigen, such as, for example, a polypeptide on the surface of the virus; indirect where a labeled second antibody is reactive with the first antibody; a competitive protocol such as would involve the addition of a labeled antigen; or sandwich where both labeled and unlabeled antibody are used, as well as other protocols well known and described in the art.

In one embodiment, an immunoassay method would utilize an antibody specific for HCV envelope determinants and would further comprise the steps of contacting a biological sample with the HCV-specific antibody and then detecting the presence of HCV material in the test sample using one of the types of assay protocols as described above. Polypeptides and antibodies produced as described herein may also be supplied in the form of a kit, either present in vials as purified material, or present in compositions and suspended in suitable diluents as previously described.

In a preferred embodiment, such a diagnostic test kit for detection of HCV antigens in a test sample comprises in combination a series of containers, each container a reagent needed for such assay. Thus, one such container would contain a specific amount of HCV-specific antibody as already described, a second container would contain a diluent for suspension of the sample to be tested, a third container would contain a positive control and an additional container would contain a negative control. An additional container could contain a blank.

For all prophylactic, therapeutic and diagnostic uses, the antibodies described herein and other reagents, plus appropriate devices and accessories, may be provided in the form of a kit so-as to facilitate ready availability and ease of use.

Screening and Diagnostic Embodiments

Embodiments also relate to the use of nucleic acid sequences and polypeptides described herein to screen potential antiviral agents for antiviral activity against HCV. Generally, the antiviral agents are tested at a variety of concentrations, for their effect on preventing viral replication in cell culture systems which support viral replication, and then for an inhibition of infectivity or of viral pathogenicity (and a low level of toxicity) in an animal model system. In one embodiment, animal cells (especially human cells) transfected with the nucleic acid sequences described herein are cultured in vitro and the cells are treated with a candidate antiviral agent (a chemical, peptide etc.) by adding the candidate agent to the medium. The treated cells are then exposed, possibly under transfecting or fusing conditions known in the art, to the nucleic acid sequences of the present invention. A sufficient period of time would then be allowed to pass for infection to occur, following which the presence or absence of viral replication would be determined versus untreated control cells by methods known to those of ordinary skill in the art.

Such methods include, but are not limited to, the detection of viral antigens in the cell, for example, by immunofluorescence procedures well known in the art; the detection of viral polypeptides by Western blotting using antibodies specific therefor; the detection of newly transcribed viral RNA within the cells by RT-PCR; and the detection of the presence of live, infectious virus particles by injection of cell culture medium or cell lysates into healthy, susceptible animals, with subsequent exhibition of the signs and symptoms of HCV infection. A comparison of results obtained for control cells (treated only with nucleic acid sequence) with those obtained for treated cells (nucleic acid sequence and antiviral agent) would indicate, the degree, if any, of antiviral activity of the candidate antiviral agent. Of course, one of ordinary skill in the art would readily understand that such cells can be treated with the candidate antiviral agent either before or after exposure to the nucleic acid sequence of the present invention so as to determine what stage, or stages, of viral infection and replication said agent is effective against.

In an alternative embodiment, viral enzyme such as NS3 protease, NS2-NS3 protease, NS3 helicase or NS5B RNA polymerase may be produced from a nucleic acid sequence described herein and used to screen for inhibitors which may act as antiviral agents. The structural and nonstructural regions of the HCV genome, including nucleotide and amino acid locations, have been determined, for example, as depicted in Houghton, M. 1996 Hepatitis C viruses. In *Fields Virology* (B. N. Fields, D. M. Knipe, P. M. Howley, et al., Eds.), Third ed., pp. 1035-1058. Lippincott-Raven Publishers, Philadelphia, FIG. 1; and Major, M. E. et al. (1997), Table 2.

Such above-mentioned protease inhibitors may take the form of chemical compounds or peptides which mimic the known cleavage sites of the protease and may be screened using methods known to those of skill in the art (Houghton, M. 1996 Hepatitis C viruses. In *Fields Virology* (B. N. Fields, D. M. Knipe, P. M. Howley, et al., Eds.), Third ed., pp. 1035-1058. Lippincott-Raven Publishers, Philadelphia; and Major, M. E. et al. 1997).

For example, a substrate may be employed which mimics the protease's natural substrate, but which provides a detectable signal (e.g., by fluorimetric or calorimetric methods such as luciferase or green fluorescent protein) when cleaved. This substrate is then incubated with the protease and the candidate protease inhibitor under conditions of suitable pH, temperature etc. to detect protease activity. The proteolytic activities of the protease in the presence or absence of the candidate inhibitor are then determined.

In yet another embodiment, a candidate antiviral agent (such as a protease inhibitor) may be directly assayed in vivo for antiviral activity by administering the candidate antiviral agent to an animal transfected with a nucleic acid sequence described herein or infected with a virus as described herein and then measuring viral replication in vivo via methods such as RT-PCR. Of course, the animal may be treated with the candidate agent either before or after transfection with the infectious nucleic acid sequence or infected with a virus as described herein so as to determine what stage, or stages, of viral infection and replication the agent is effective against.

In other embodiments, the nucleic acids described herein are used to produce viral enzymes such as NS3 protease, NS2-NS3 protease, NS3 helicase or NS5B RNA polymerase for use in diagnostic and screening assays to detect the proteolytic activities of the viral enzymes. Fluorometric and colorometric assays as described above are known in the art.

Also provided herein are methods of identification of a subject in need of an immune response to HCV. For example, in such embodiments, a biological sample is obtained from a subject (e.g., a human) having RNA or protein, and a diagnostic assay is performed on said subject to measure the level of HCV or anti-HCV antibodies present in the subject. Diagnostic assays for HCV are known and can include the use of anti-HCV antibodies as described above, which can be used as in vitro diagnostic agents to test for the presence of HCV in biological samples taken from animals, especially humans. Such assays include, but are not limited to, radioimmunoassays, EIA, fluorescence, Western blot analysis and ELISAs. inoculation with an immunogen as described herein.

Embodiments also include the nucleic acid sequences, viruses and polypeptides described herein supplied in the form of a kit, alone or in the form of a pharmaceutical composition.

All scientific publication and/or patents cited herein are specifically incorporated by reference.

The following examples illustrate various aspects of the invention but are in no way intended to limit the scope thereof.

EXAMPLES

Example 1

This example provides greater detail on some of the materials and methods employed in the experiments described herein.

Source of HCV strain HC-TN. HCV strain HC-TN was from a patient who developed fulminant hepatic failure twice after liver transplantation for cryptogenic liver cirrhosis (Farci, P. et al. 1999 *J. Infect. Dis.* 179:1007-1011); she apparently became infected with HCV after receiving red blood cells before transplantation. A chimpanzee (CH1422) was inoculated with 100 μl of serum obtained 5 days before the first liver transplantation (see FIG. 1A) (Id.). (The data in FIG. 1A were adapted from Farci et al. [Id.], but the qualitative and quantitative HCV RNA tests were performed in this study.) A pool of HC-TN virus was made from plasmapheresis units collected from CH1422 during weeks 4 to 6 post inoculation.

Amplification, cloning, and sequence analysis. RNA extracted from 100-μl aliquots of the HC-TN pool with a RNA preparation kit, TRIZOL® LS system (LIFE TECHNOLOGIES®, Gaithersburg, Md.) was denatured at 65° C. for 2 min. HCV cDNA was synthesized at 42° C. for 1 h with SUPERSCRIPT®II reverse transcriptase (LIFE TECHNOLOGIES®) and specific reverse primers. The cDNA was treated with RNase H and RNase T1 (LIFE TECHNOLOGIES®). To clone the entire open reading frame (ORF), a one-round long PCR was performed using an Advantage PCR polymerase mix (CLONTECH®, Palo Alto, Calif.). Gel-purified amplicons were A tailed with Taq DNA polymerase (LIFE TECHNOLOGIES®) at 72° C. for 1 h and cloned into pCR2.1-TOPO (INVITROGEN®, Carlsbad, Calif.). DH5α-competent cells (LIFE TECHNOLOGIES®) were transformed and selected on LB agar plates containing 100 μg/ml ampicillin (STRATAGENE®, La Jolla, Calif.) and amplified in LB liquid cultures at 30° C. (Id.). A region spanning from nonstructural 5B (NS5B) to the conserved region of the 3' untranslated region (UTR) was amplified by nested PCR with an Advantage 2 PCR polymerase mix and cloned as described previously (Yanagi, M. et al. 1997 *Proc. Natl. Acad. Sci. USA* 94:8738-8743, the entirety of which is incorporated by reference herein). Final DNA preparations were sequenced using standard procedures.

The 5' terminus was amplified from serum by 5' rapid amplification of cDNA ends (RACE) with dC or dA tailing (LIFE TECHNOLOGIES®) and three antisense C primers (615R [5'-CGCAACCCTCATTGCCATAG-3' (SEQ ID NO: 3)] for reverse transcription [RT], 519R [5'-CTCGAGGT-TGCGACCGCTCGGAAG-3' (SEQ ID NO: 4)] for the first PCR, and 433R+Kpn-I [5'-CGGGGTACCACGATCTGAC-CGCCACCCGGGAAC-3' (SEQ ID NO: 5)] for the second PCR). To determine the 3'-terminal sequence, the 5' end of the negative-strand HCV RNA extracted from liver homogenate obtained from CH1581 was amplified by 5' RACE with dC tailing and specific primers (−351R [5'-TGGTTCACG-GCTGGCTACAG-3' (SEQ ID NO: 6)] for RT, −334R [5'-CAGCGGGGGAGACATTTATCACAG-3' (SEQ ID NO: 7)] for the first PCR, and −315R [5'-CACAGCGTGTCTCAT-GCCCGGCCC-3' (SEQ ID NO: 8)] for the second PCR). The PCR products were cloned into pCR2.1-TOPO (INVITROGEN®).

To determine the consensus sequence of the entire ORF of HC-TN recovered from chimpanzees, two procedures were used. In serum samples with titers of >$10^5$ IU/ml, long RT-PCR was performed, followed by nested PCR with genotype 1a-specific primers of 10 fragments. In samples with titers of <$10^5$ IU/ml, RT-nested PCR was performed, with Taq Gold DNA polymerase (PERKIN ELMER®, Wellesley, Mass.) (Bukh, J. et al. 1998 *J. Infect. Dis.* 178:1193-1197), of 19 fragments by use of 1a-specific primers. The numbers of observed synonymous substitutions (ds) and nonsynonymous substitutions (dn) and the ratios of synonymous to nonsynonymous substitutions (ds/dn) were calculated using the SynSCAN program.

Full-length consensus cDNA clone of HC-TN. pHC-TN was constructed by standard molecular techniques using three clones that contained the ORF, one clone that contained the variable and poly(U-UC) regions of the 3' UTR, and pCV-H77C. Large-scale preparation of a single clone was performed with a QIAGEN® (Valencia, Calif.) Endofree maxi kit. The final DNA had the expected sequence.

Experimental infection of chimpanzees. The housing and care of chimpanzees were in compliance with relevant guidelines and requirements (National Research Council. 1996. Guide for the care and use of laboratory animals. National Academy Press, Washington, D.C.). CH1581 was inoculated intravenously with dilutions of the CH1422 pool. CH1579 was inoculated intrahepatically by a percutaneous procedure (Yanagi, M. et al. 1998 *Virology* 244:161-172) with RNA transcribed by T7 RNA polymerase (PROMEGA®, Madison, Wis.) from 20 µg of XbaI-digested pHC-TN. Serum samples were collected once or twice weekly and tested for HCV RNA (Monitor 2.0; ROCHE DIAGNOSTICS®, Indianapolis, Ind.), HCV antibodies (ELISA 2.0; ABBOTT®, Chicago, Ill.), and alanine aminotransferase (ALT) (Anilytics, Gaithersburg, Md.). Monitor-negative samples were tested by a more sensitive RT-nested PCR (Bukh, J. et al. 1998 *J. Infect. Dis.* 178:1193-1197). Samples obtained by weekly liver biopsies were examined for necroinflammatory changes (Bukh, J. et al. 2002 *Proc. Natl. Acad. Sci. USA* 99:14416-14421).

Anti-E1 was tested for using an enzyme-linked immunosorbent assay (ELISA) with recombinant E1 protein (amino acids [aa] 192 to 329) expressed from strain H77 (Bartosch, B. et al. 2003 *Proc. Natl. Acad. Sci. USA* 100:14199-14204; Meunier, J. C. et al. 2005 *Proc. Natl. Acad. Sci. USA* 102: 4560-4565) and for anti-E2 by use of an ELISA with recombinant E2 protein (aa 388 to 664) of strain H, provided by I. K. Mushahwar (Abbott) (Lesniewski, R. R. et al. 1995 *Princess Takamatsu Symp.* 25:129-137; Meunier, J. C. et al. 2005 *Proc. Natl. Acad. Sci. USA* 102:4560-4565). Antibodies against E2 HVR1 were assayed with an ELISA using a biotinylated HC-TN-specific peptide (aa 384 to 410) (Meunier, J. C. et al. 2005 *Proc. Natl. Acad. Sci. USA* 102:4560-4565). The percent neutralization in postinfection sera, compared with that in the preinoculation sample, was determined with a retroviral HCV pseudovirus assay using ppH77(1a), as described in detail previously (Id.).

The details of protocols used to detect cellular immune responses were published previously (Thimme, R. et al. 2002 *Proc. Natl. Acad. Sci. USA* 99:15661-15668; Thimme, R. et al. 2001 *J. Exp. Med.* 194:1395-1406). Peripheral blood mononuclear cells (PBMC) were isolated from 40 ml of blood. Liver-infiltrating lymphocytes were isolated from liver tissue obtained by needle biopsy. Cell suspensions were incubated with magnetic beads coupled to anti-CD4 or anti-CD8, and bound CD4$^+$ or CD8$^+$ T cells were isolated using a magnetic particle concentrator and next expanded for 2 weeks. PBMC or polyclonally expanded CD4$^+$ T cells were tested for HCV-specific proliferative capacity after 6 days of culture with HCV-1 proteins (C22, C33-c, c100, and NS5). $^3$H[thymidine] was added for 16 h, and the mean levels of thymidine incorporation in the HCV protein-stimulated and control cultures were used to calculate the stimulation indexes (SI); values of >2.0 were considered positive. Polyclonally expanded CD8$^+$ T cells were tested by intracellular gamma interferon staining after 5 h of stimulation with autologous Epstein-Barr virus-immortalized B-cell lines that were infected with recombinant HCV H77-encoding vaccinia viruses vHCV(1-1488) or vHCV(827-3011) together with VTF7, provided by C. M. Rice (Rockefeller University, New York, N.Y.), or with VTF7 alone. The frequency of HCV-specific CD8$^+$ T cells was defined as the percentage of CD8$^+$ T cells that produced gamma interferon in response to stimulation by B-cell lines coinfected by vHCV and VTF7 after subtraction of the gamma interferon-positive, CD8$^+$ T cells detected after stimulation in the absence of vHCV.

Transfection of Huh7.5 cells with RNA transcripts from pHC-TN. Huh7.5 cells, provided by C. M. Rice (Rockefeller University, New York, N.Y.), were maintained in growth medium consisting of complete Dulbecco's modified Eagle's medium (GIBCO BRL®, Gaithersburg, Md.) supplemented with 10% heat-inactivated fetal bovine serum, 50 IU/ml penicillin G, and 50 µg/ml streptomycin. Cells were incubated at 37° C. in a humidified 5% $CO_2$ incubator. RNA was transcribed, as described above, from pJFH1 and pHC-TN digested with XbaI; the pJFH1 plasmid was provided by Takaji Wakita (Tokyo Metropolitan Institute for Neuroscience, Tokyo, Japan).

Transfection was performed using a DMRIE-C reagent (INVITROGEN®) in six-well plates (4×$10^5$ Huh7.5 cells/well). Briefly, cells were washed with 2 ml of Opti-MEM I medium (GIBCO®). Eight microliters of DMRIE-C reagent was first diluted in 1 ml of Opti-MEM I medium before the addition of a transcription mixture containing approximately 3 µg of RNA transcripts (based on gel analysis). Finally, the complexed RNA was incubated with the washed Huh7.5 cells at 37° C. for 4 h and the medium was replaced with complete growth medium. For immunofluorescence staining with mouse anti-HCV core protein monoclonal antibody (B2) (Anogen, Mississauga, Ontario, Canada), the Huh7.5 cells were trypsinized, transferred to eight-well chamber slides, and incubated at 37° C. overnight. The cells were washed twice with phosphate-buffered saline (PBS) and fixed and permeabilized with acetone for 3 min. Twenty-five microliters of a 1/200 dilution (in 5% bovine serum albumin in PBS) of the HCV anticore antibody was added to each grid and incubated at room temperature for 20 min. After a wash with PBS, a 1/100 dilution of the secondary antibody, anti-mouse immunoglobulin G (heavy plus light chains) fluorescein isothiocyanate-conjugated antibody (PIERCE®), was added to each grid and incubated at room temperature for 3 min. A drop of VECTASHIELD®, a chemical mixture for the retardance of photobleaching of flourochromes containing DAPI (4',6'-diamidino-2-phenylindole) was added to each grid of cells to stain nuclei. Slides were read with an Axioscope 2 Plus fluorescence microscope (ZEISS®).

Example 2

Isolation of HCV Genotype 1a (HC-TN)

Figure 1A:
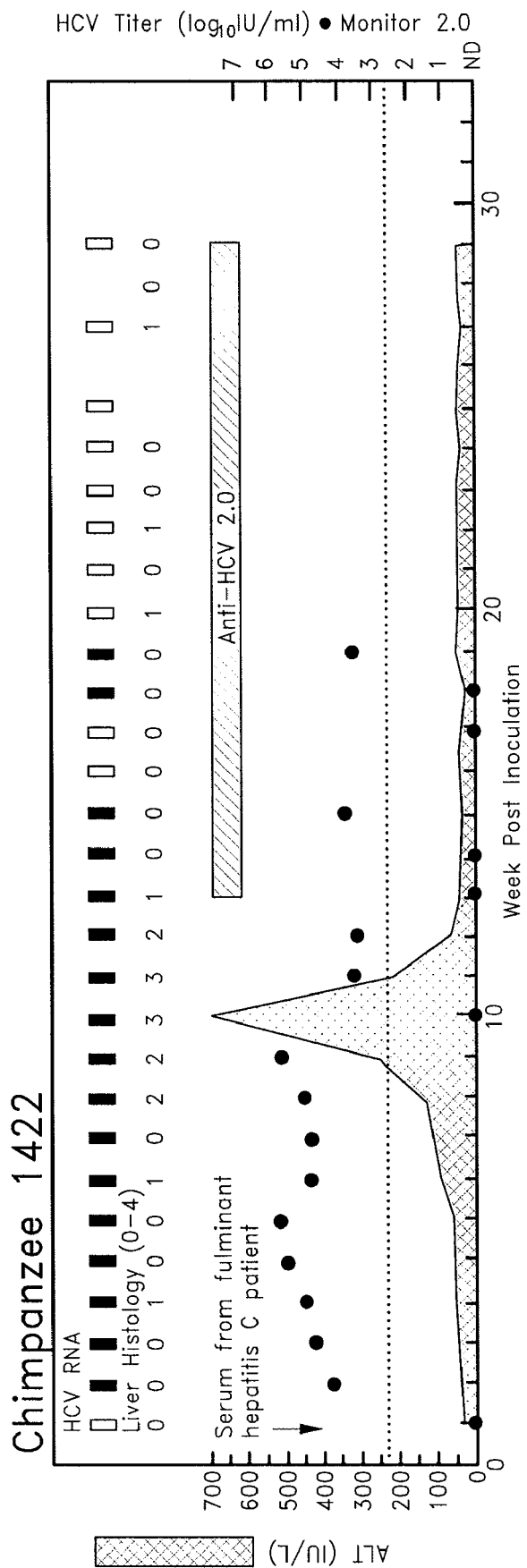
FIG. 1 shows the course of infection with HCV strain HC-TN in (A) CH1422 (first-passage polyclonal infection), (B) CH1581 (second-passage quasipolyclonal infection), and (C) CH1579 (pHC-TN monoclonal infection). Serum samples collected once or twice weekly were tested for HCV RNA by an in-house RT-nested PCR with 5' UTR primers and/or by use of a Roche Monitor 2.0 test. Filled rectangles denote positive by RT-nested PCR and/or by Monitor; white rectangle denotes negative by RT-nested PCR in two independent assays. The circles represent HCV Monitor titers; samples below the detection limit of 600 IU/ml (indicated by the dotted line) are shown as not detected (ND). Seroconversion in the second-generation ELISA is represented by a horizontal bar. Shaded area represents serum alanine aminotransferase (ALT). For liver histology, necroinflammatory changes of liver biopsy samples are graded 0 (normal), 1 (mild), 2 (mild to moderate), 3 (moderate to severe), or 4 (severe).
Figure 1B:
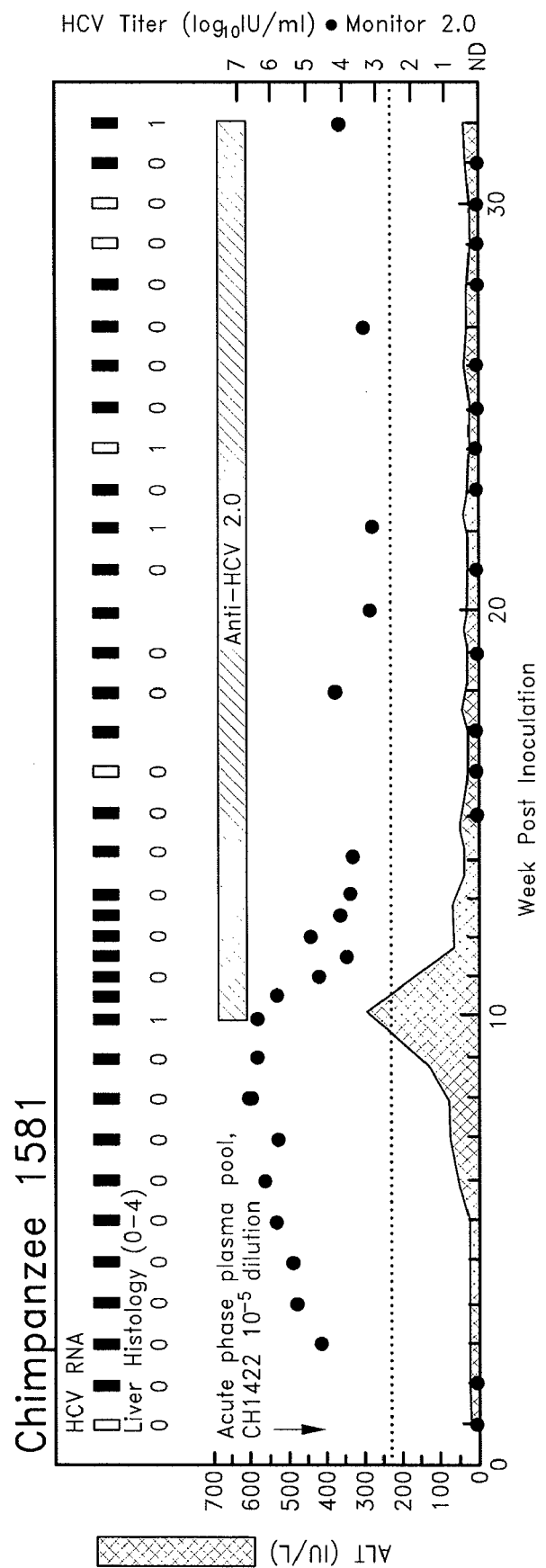
Figure 1C:
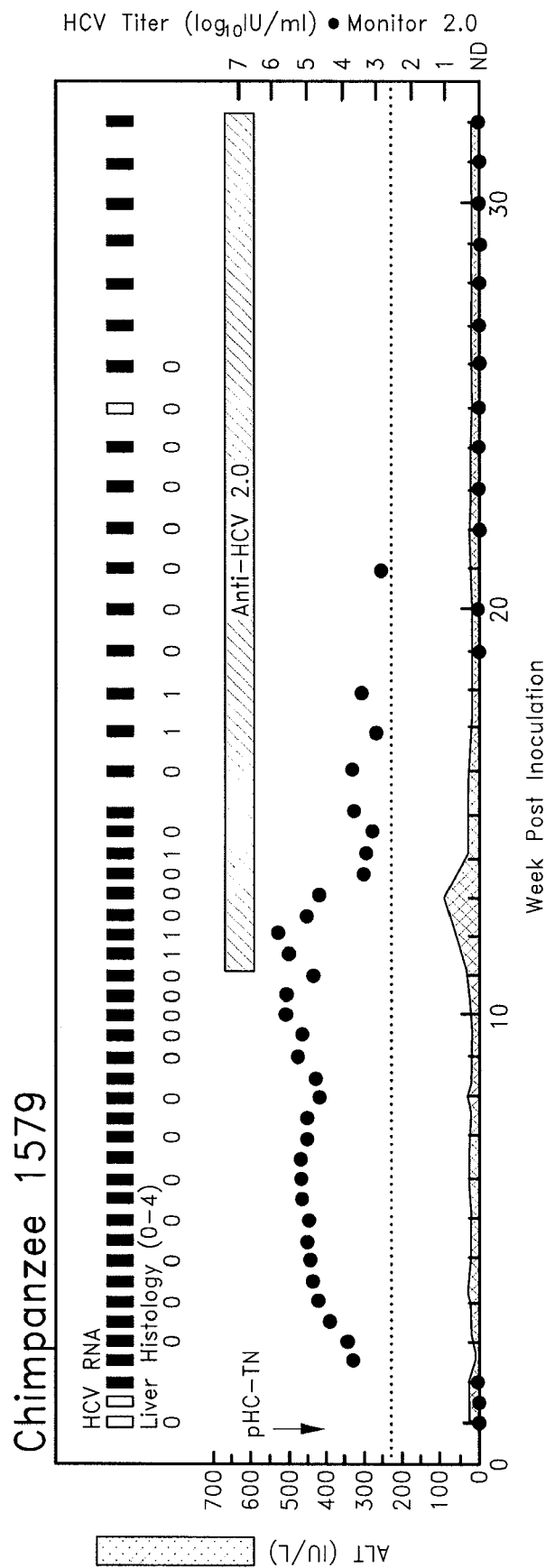

A genotype 1a strain (HC-TN) of HCV recovered from a patient who developed fulminant hepatic failure was studied (Farci, P. et al. 1999 *J. Infect. Dis.* 179:1007-1011). Following transmission to CH1422, it caused severe hepatitis, with an ALT peak of 744 IU/liter and with an unusually pronounced necroinflammatory activity in liver biopsy samples (FIG. 1A). Serum HCV titers reached $10^5$ to $10^{5.5}$ IU/ml during weeks 4 to 9, followed by a dramatic decrease and clearance during week 20. No remaining sera was available from the patient used to inoculate CH1422. Thus, to further investigate the phenotype of the HC-TN strain, a second passage was performed, this time to CH1581 (FIG. 1B). Furthermore, a full-length consensus cDNA clone was constructed, the infectivity of which was confirmed in CH1579 (FIG. 1C), to study the phenotype of monoclonal infection with this particular HCV strain.

Example 3

Genetic Analysis of Strain HC-TN

Figure 2:
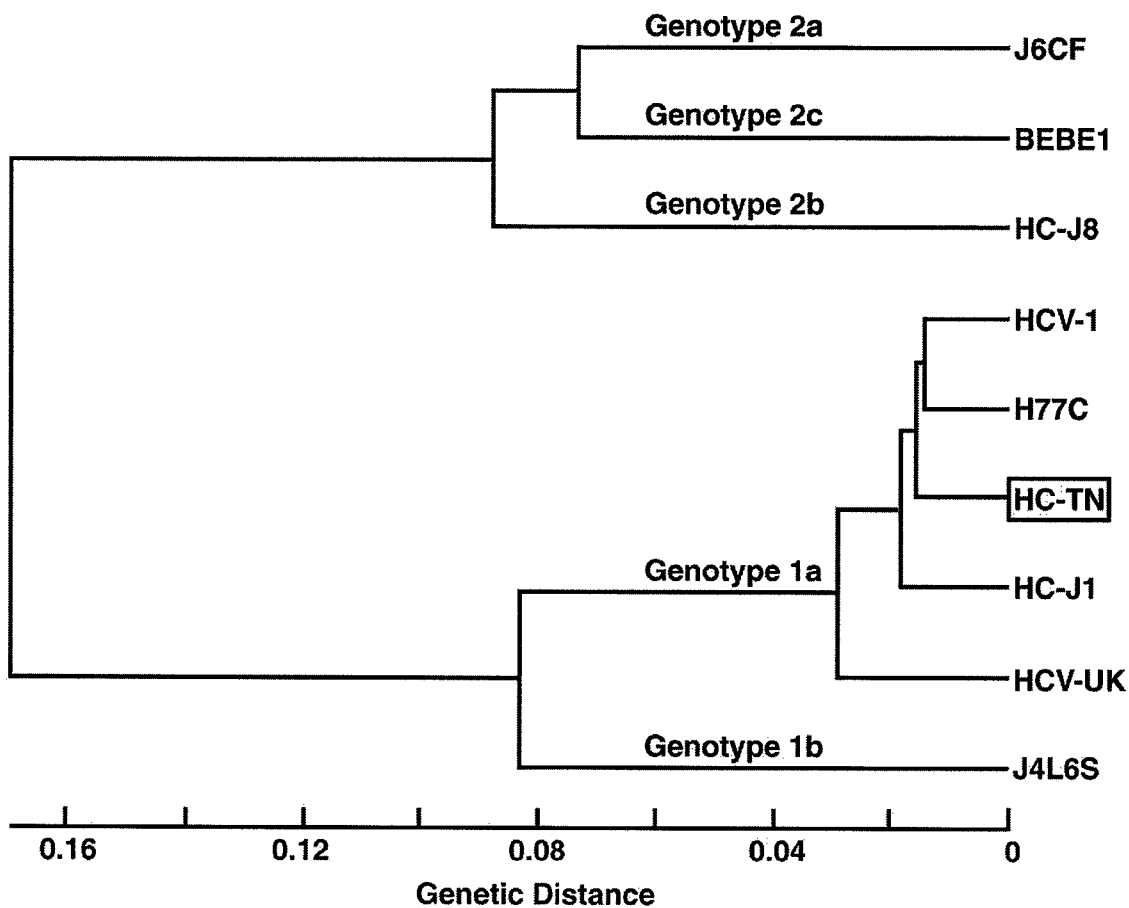
FIG. 2 shows tree analysis of predicted polyprotein sequences of HC-TN (boxed) and other HCV strains. The multiple sequence alignment and tree analysis were performed with GeneWorks (Bukh, J., et al., 1995 *Semin. Liver Dis.* 15:41-63).

The HC-TN sequence from the CH1422 plasma pool was analyzed. To determine the consensus ORF, direct sequencing was performed on amplicons obtained by long RT-PCR followed by PCR of 10 overlapping fragments. In addition, three clones obtained from the long-RT-PCR amplicons were analyzed. The ORF consisted of 9,033 nt encoding 3,011 aa. The genome population in CH1422 was virtually homogeneous, since heterogeneity was found among the three clones at only 26 (0.29%) nucleotide and 20 (0.66%) amino acid positions. Also, the clones had identical sequences within HVR1. The consensus sequence deduced from the ORF clones was identical to that obtained by direct sequencing. It differed from those of other 1a strains (Choo, Q. L. et al. 1991 *Proc. Natl. Acad. Sci. USA* 88:2451-2455; Kumar, U. et al. 2000 *J. Viral Hepat.* 7:459-465; Okamoto, H. et al. 1992 *Nucleic Acids Res.* 20:6410; Yanagi, M. et al. 1997 *Proc. Natl. Acad. Sci. USA* 94:8738-8743) by 4.3% to 8.0% and by 2.9% to 5.4% at the nucleotide and amino acid levels, respectively (FIG. 5). A tree analysis of the polyprotein sequence of representative HCV isolates (Choo, Q. L. et al. 1991 *Proc. Natl. Acad. Sci. USA* 88:2451-2455; Kumar, U. et al. 2000 *J. Viral Hepat.* 7:459-465; Nakao, H. et al. 1996 *Arch. Virol.* 141:701- 704; Okamoto, H. et al. 1992 *Nucleic Acids Res.* 20:6410; Okamoto, H. et al. 1992 *Virology* 188:331-341; Yanagi, M. et al. 1999 *Virology* 262:250-263; Yanagi, M. et al. 1997 *Proc. Natl. Acad. Sci. USA* 94:8738-8743; Yanagi, M. et al. 1998 *Virology* 244:161-172) showed that HC-TN was most closely related to the prototype strains HCV-1 and H77 (FIG. 2). Since the polyprotein cleavage sites were highly conserved among the 1a strains, the HC-TN gene products are predicted to be the same as those of strain H77 (Grakoui, A. et al. 1993 *J. Virol.* 67:1385-1395; Lin, C. et al. 1994 *J. Virol.* 68:5063-5073).

To analyze the 5' UTR of HC-TN, 5' RACE and sequencing was performed on 10 and 3 clones (nucleotides [nt] 1 to 409) obtained following dC and dA tailing, respectively. All clones had identical 5'-terminal sequences, and the remainder of the 5' UTR was highly conserved. The HC-TN 5' UTR sequence was identical to that of HCV-1 (Han, J. H. et al. 1991 *Proc. Natl. Acad. Sci. USA* 88:1711-1715). To analyze the 3' UTR, sequencing was performed on 12 clones of PCR products, which included the variable and the poly(U-UC) regions. The variable region consisted of 43 nt (nt 9375 to 9417), including two in-frame termination codons. All clones had identical sequences except at position 9391 (11 C, 1 T). The poly(U/UC) regions varied in length (76 to 148 nt), entirely due to variation of the poly(U) regions (41 to 113 nt). The poly(UC) regions had the same length (35 nt), and the sequences (5'-CUUUUUCCCUCUUUUUCUUCUCUUUUUC-CUUCUUU-3' (SEQ ID NO: 9)) were identical in all 12 clones except at position 3 11 U, 1 C). Furthermore, it was found that this region had the same sequence in the five clones from negative-strand RNA extracted from CH1581 liver. The sequence of the conserved region was determined by 5' RACE (dC tailing) on the negative-strand RNA extracted from CH1581 liver homogenate collected at week 8. Five clones (nt 9410 to the 3' terminus) analyzed had the same 3'-terminal sequences, and the consensus sequence (101 nt) was identical to that of strain H77 (Kolykhalov, A. A. et al. 1996 *J. Virol.* 70:3363-3371).

Example 4

Infectivity Titration of HC-TN Plasma Pool

The pool collected from CH1422 during weeks 4 to 6 had an HCV genome titer of ~$10^5$ IU/ml (Monitor 2.0, $10^{5.3}$ IU/ml; Versant HCV RNA b-DNA 3.0 [BAYER®, Tarrytown, N.Y.], $10^{5.0}$ IU/ml). Its infectivity titer was determined by reverse titration in CH1581. The $10^{-6}$ dilution was noninfectious. However, HCV was transmitted to CH1581 by inoculation of 1 ml of a $10^{-5}$ dilution (FIG. 1B), indicating an infectivity titer of ~$10^5$ chimpanzee infectious doses/ml. Analysis was performed on the ORF of HCV recovered from the serum of CH1581 at week 8. Differences between the CH1581 sequence and the consensus sequence of the CH1422 virus used as the inoculum were found at only two nucleotide positions (A1535G and G6531A) and resulted in one NS5A amino acid change (A2064T). Both substitutions were also found at week 1.

Figures 1, 3B:
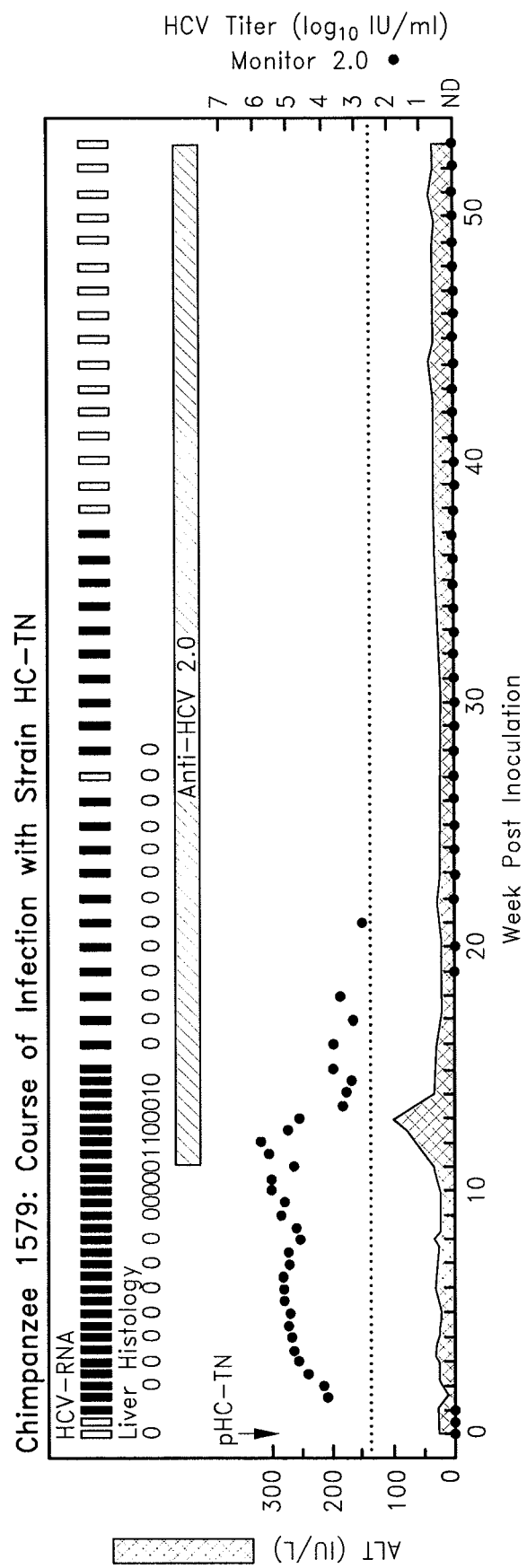
Figure 3B:
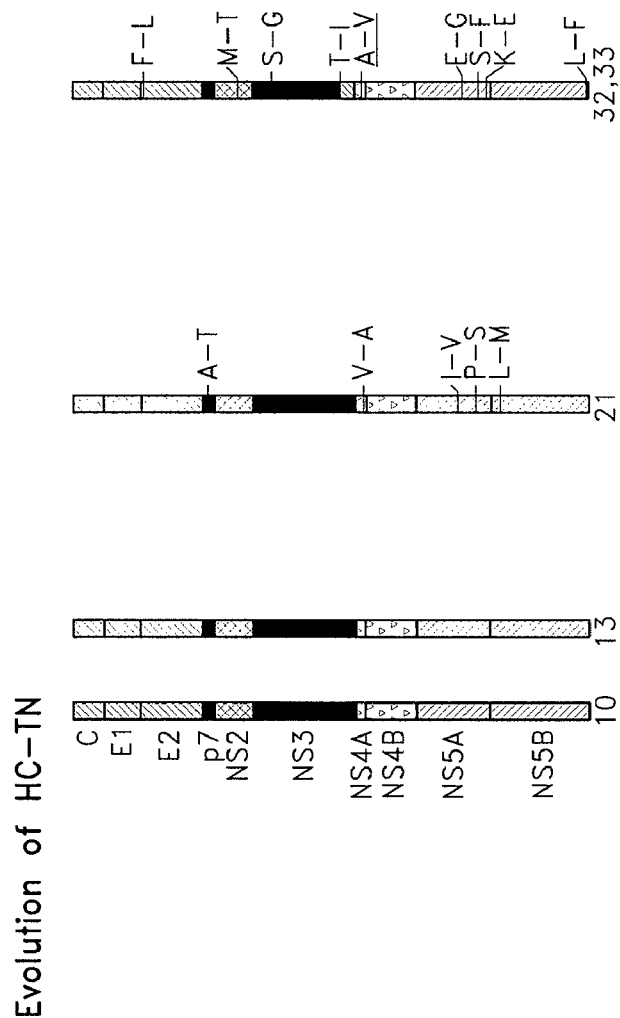
Figure 2:
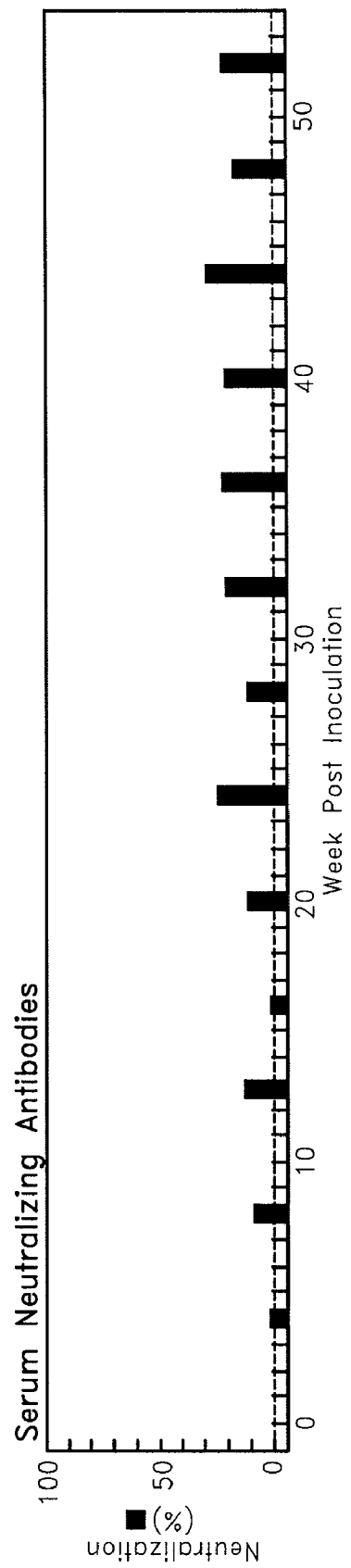
Figures 3, 3B:
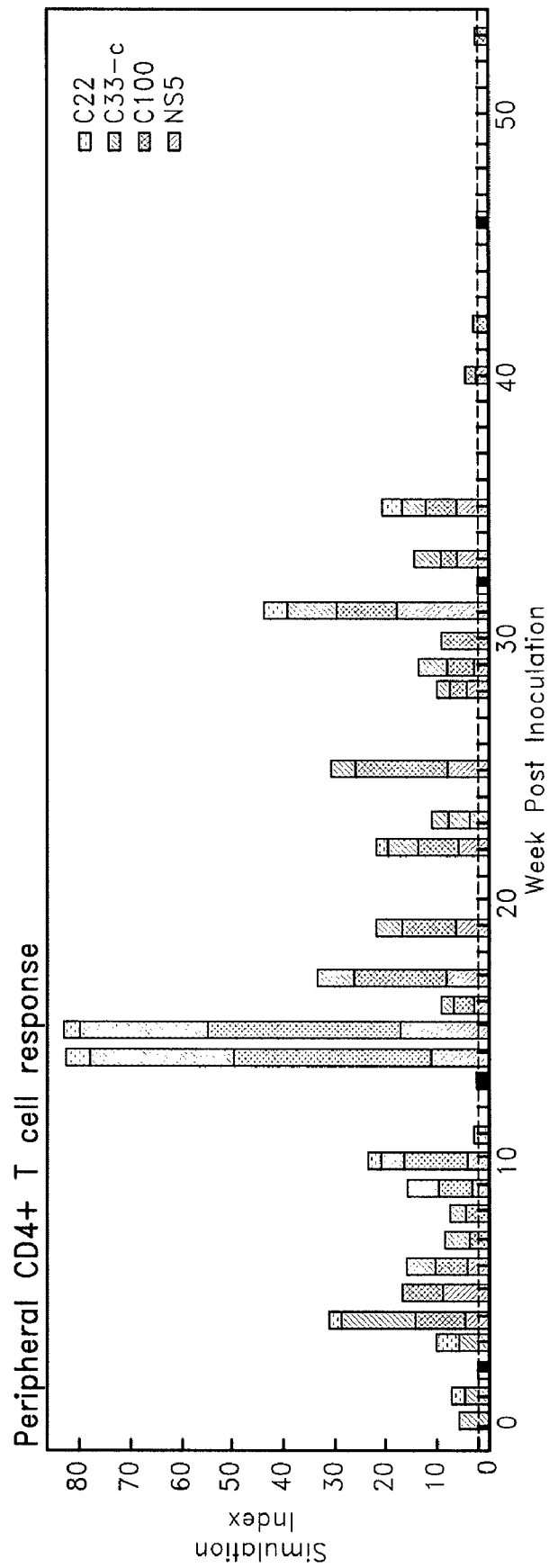
Figures 3, 3B, 4:
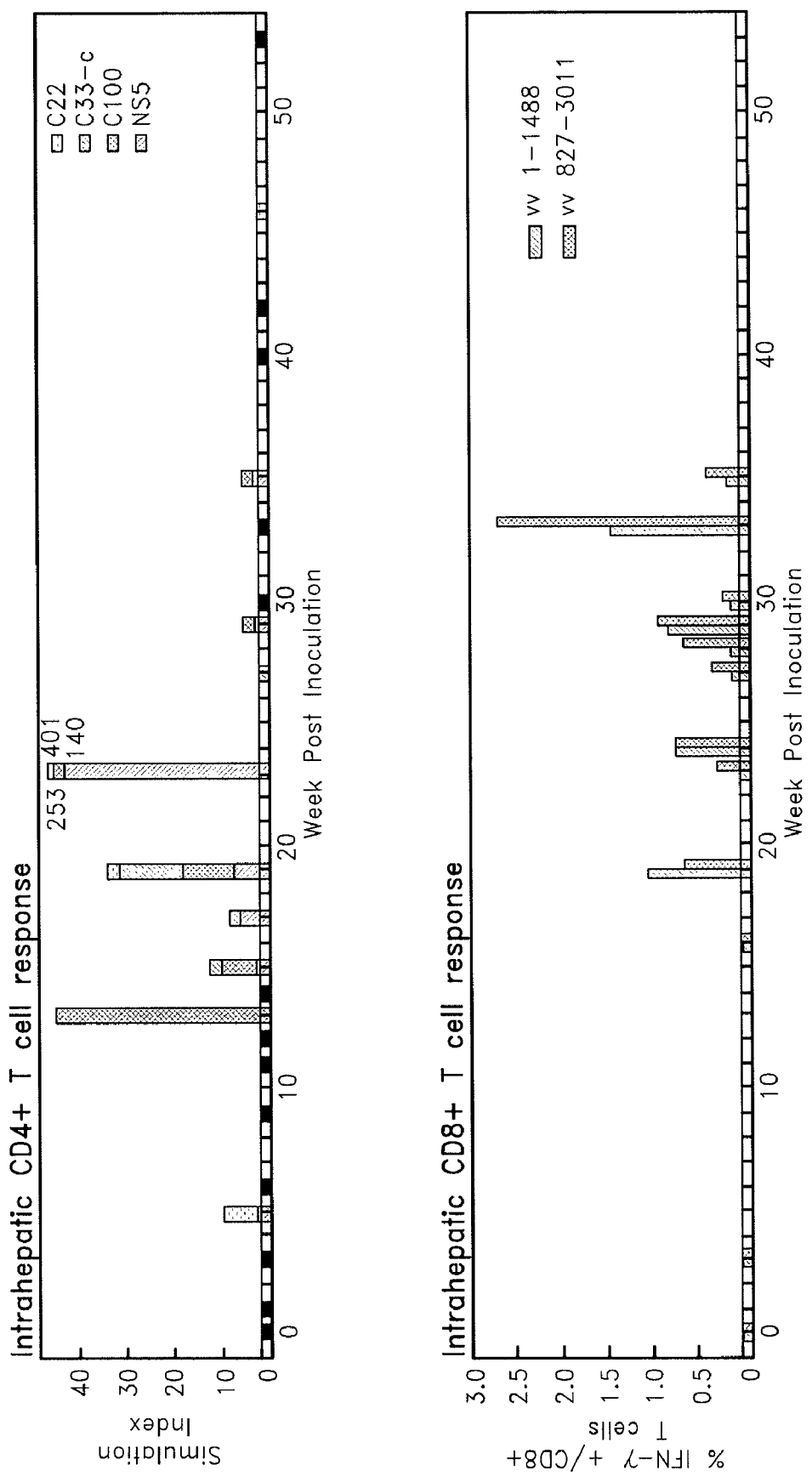
Figure 4:
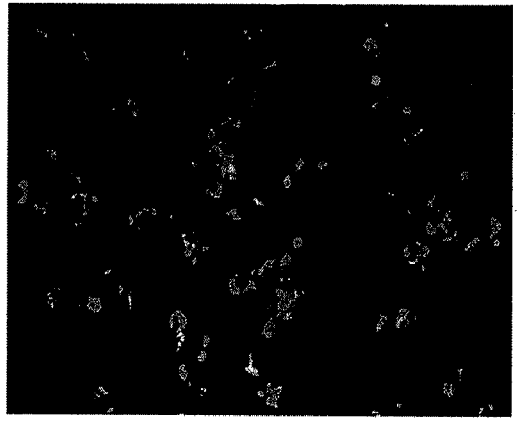
Figure 4:

In CH1581, HCV RNA titers peaked at ~$10^6$ IU/ml during weeks 5 to 10, followed by a 3-$\log_{10}$ decrease in viremia titers during weeks 10 to 15 (FIG. 3A). The titers were frequently below the detection limit of the Monitor test ($10^{2.8}$ IU/ml) during weeks 15 to 37. Furthermore, a sensitive RT-nested PCR test was negative at weeks 16, 24, 29, and 30, and during weeks 38 to 52, the HCV titers remained at $10^3$ to $10^4$ IU/ml. The second-generation ELISA became positive at week 10. However, the animal did not develop anti-E1, anti-E2, or anti-HVR1 until after 45 weeks of follow-up (Meunier, J. C. et al. 2005 *Proc. Natl. Acad. Sci. USA* 102:4560-4565). Furthermore, the chimpanzee did not develop significant (≧50% neutralization) neutralizing antibodies during the first year of follow-up (Id.) (FIG. 3B). The chimpanzee developed acute hepatitis, with a peak ALT level of 296 IU/liter (week 10). Mild necroinflammatory changes were detected in liver biopsy samples at weeks 10, 22, and 24, as well as during the persistent phase of infection.

Example 5

RNA Transcripts from a Consensus Clone (pHC-TN) are Infectious in vivo but Not in vitro In pHC-TN, the core sequence of the T7 promoter and the consensus sequence of HC-TN (9,599 nt) were contained in the NotI/XbaI-digested pGEM-9Zf vector. It contained a 5' UTR of 341 nt, an ORF of 9,033 nt, and a 3' UTR with a variable region of 43 nt followed by an 81-nt poly(U/UC) tract (46 U, 35 UC) and a 3'-terminal conserved sequence of 101 nt. RNA transcripts of pHC-TN were percutaneously injected into the liver of CH1579. For unknown reasons, the first in vivo transfection failed. However, following a subsequent transfection 4 weeks later with new RNA transcripts, the animal became infected (FIG. 3B). The HCV ORF sequence recovered from week 10 sera was identical with that of pHC-TN. The HCV titers reached peak levels of $10^5$ to $10^{5.5}$ IU/ml during weeks 4 to 13, followed by a significant decrease. The quantitative Monitor test was negative during weeks 22 to 53. However, the qualitative RT-nested PCR test remained positive until week 37. Thus, this chimpanzee had prolonged acute resolving HCV infection. The animal became positive in the second-generation ELISA at week 11 but did not develop anti-E1, anti-E2, or anti-HVR1 antibodies. Furthermore, the animal did not develop neutralizing antibodies (Id.) (FIG. 3B). It had elevated ALT only during weeks 12 to 13 (peak, 90 IU/liter) and mild histological changes in liver biopsy samples during weeks 11 to 18.

A molecular clone of strain JFH1, also recovered from a patient with fulminant hepatitis C, was recently found to be infectious in Huh7 and Huh7.5 cells (Wakita, T. et al. 2005 *Nat. Med.* 11:791-796; Zhong, J. et al. 2005 *Proc. Natl. Acad. Sci. USA* 102:9294-9299). Huh7.5 cells were transfected with RNA transcripts from pJFH1 and pHC-TN (FIG. 4). JFH1 chimeras were also included, which contain core through NS2 from HC-TN (data not shown). Clear evidence of replication was observed with JFH1 and TN/JFH1 chimeras, but there was no evidence of HCV replication with HC-TN. The fact that replication of the TN/JFH1 chimeras could be detected by staining for core proved that the anticore used for immunofluorescence staining could readily detect the HC-TN strain; therefore, the lack of staining in cells transfected with pHC-TN indicated that this virus could not replicate in these cells. Following one transfection with RNA transcripts of pHC-TN, the culture was monitored for more than 20 weeks with no evidence of HCV replication.

Example 6

T-Cell Responses in HC-TN-Infected Chimpanzees Irrespective of the Final Outcome Analyses of the cellular immune responses were performed with CH1581 and CH1579 (FIG. 3). Cells had not been collected from CH1422. CD4+ T cells from PBMC or polyclonally expanded from liver specimens were tested for HCV-specific proliferative responses with HCV-1 proteins (C22, C33-c, c100, and NS5). Polyclonally expanded liver CD8+ T cells were tested for intracellular gamma interferon staining after coculture with autologous B cells expressing the entire H77 polyprotein from vaccinia viruses.

In CH1581, HCV-multispecific peripheral and intrahepatic CD4+ T-cell responses were detected in the liver beginning at weeks 7 and 8, respectively (FIG. 3A) (Thimme, R. et al. 2002 *Proc. Natl. Acad. Sci. USA* 99:15661-15668). These responses decreased during the period with low-titer viremia (weeks 22 to 31). Intrahepatic CD8+ T-cell responses were detected at week 9 and in the available samples tested thereafter, including samples tested during the period with low-titer viremia (FIG. 3A) (Id.). In CH1579, the peripheral HCV-multispecific CD4+ responses appeared earlier and were more vigorous than the intrahepatic CD4+ responses (FIG. 3B). In fact, multispecific CD4+ responses against core, NS3, NS4, and NS5 proteins were detected during weeks 1 to 35. In contrast, intrahepatic multispecific CD4+ T-cell responses against core, NS3, NS4, and NS5 proteins were detected primarily during the initial decrease of viremia titers during weeks 13 to 23. The strongest intrahepatic CD4+ response observed in the present study occurred at week 23 in CH1579. Weaker intrahepatic CD4+ responses were observed during the following period with low-titer viremia. Vigorous intrahepatic CD8+ T-cell responses were observed during the low-titer-viremia period that preceded viral clearance (FIG. 3B). A reproducible CD8+ T-cell response against selected epitopes in either animal was undetectable, owing to the apparent low frequency of that response in the periphery (data not shown). Overall, it was found that both animals had vigorous HCV-specific T-cell responses during the dramatic decrease in HCV titers and that these responses were sustained while viremia was present.

Example 7

Repeated Emergence of New Virus Variants During the Host Immune Response

The entire ORF of viruses recovered from the three chimpanzees was sequenced, each at multiple time points (FIGS. 6, 7 and 8). For CH1422, analysis was performed on the HCV sequence from the pool taken at peak viremia titers (weeks 4 to 6) as well as that from a serum sample taken at week 19, after the virus became transiently undetectable at weeks 16 and 17 (FIG. 1A). 78 nucleotide and 17 amino acid substitutions at week 19 were detected. The relatively high mutation rate and ds/dn ratio compared with those of CH1581 and CH1579 (FIG. 6) suggested that the virus that reemerged represented the selection of a preexisting minor variant. The amino acid changes were located in core (G187V), E2 (I438V and S453P), p7 (L765V and L790F), NS2 (V873I, V879I, and K927N), NS3 (L1504P), NS4B (A1832T), NS5A (K2016R, Q2095R, E2228G, L2340P, and K2414E), and NS5B (H2483Y and T2810I).

During the first 11 weeks, prior to the initial decrease in virus titers, the sequence for CH1581 remained unchanged, but at each subsequent week tested, new variants emerged (FIGS. 3A, 6 and 7). The mutation rates observed to occur between two subsequent time points thereafter ranged from $3.38 \times 10^{-3}$ to $24.47 \times 10^{-3}$ and $6.91 \times 10^{-3}$ to $34.53 \times 10^{-3}$ substitutions/site/year at the nucleotide and amino acid levels, respectively, and the ds/dn ratios were relatively low during the first year. Twenty amino acid changes were maintained by week 52. Only one of these, K2414E, was detected also in CH1422. The first four changes, including a change in p7, occurred at week 14. At week 18, five additional changes occurred in NS2, NS4B, NS5A, and NS5B. It is noteworthy that three changes observed at week 14 within the nonstructural proteins, in which the original sequence was present as a minor species, had reverted to the initial sequence at week 18. To rule out that these changes observed only at week 14 did not represent PCR or sequencing errors, the genome regions with these mutations from the week 14 sample, as well as from a week 13 sample reamplified and sequenced (FIG. 7). All three changes were confirmed at week 14, and one change was present also at week 13. A virus with six additional mutations, in E2 (outside HVR1), p7, NS2, and NS5A, emerged at week 27. This included a new change at the p7 position that had occurred at week 14. During weeks 32 to 52, changes were observed at each time point analyzed. They were located within E2, p7, NS2, NS3, NS5A, and NS5B. They included a single HVR1 change at week 45.

Changes were not found in CH1579 during the first 13 weeks of follow-up (FIGS. 3B and 8). The mutation rates observed thereafter were high, and the ds/dn ratios were low (FIG. 6). Twelve amino acid changes, located in E2 (within HVR1), p7, NS2, NS3, NS5A, and NS5B, had emerged by week 32, and the identical sequence was also present at week 33. A single mutation in NS5A (K2414E) was also identified in CH1422 and CH1581. Another NS5A mutation (P2341S) was found to occur in CH1581. Since CH1579 was infected from RNA transcripts of an infectious clone, these mutations could not have originated from the original source virus but evolved de novo in this animal. Four mutations, located in p7, NS5A, and NS5B, existed already at week 21; one mutation detected in NS4A changed to the original sequence at week 32. However, it was found that this mutation was also present at week 20, confirming that it was not an artifact.

It is not known whether infection with particular HCV strains is associated with severe forms of acute hepatitis C. It was previously reported that infection with strain HC-TN (genotype 1a) was associated with fulminant hepatic failure and, following transmission to a chimpanzee, caused unusually severe acute hepatitis (Farci, P. et al. 1999 *J. Infect. Dis.* 179:1007-1011). In the present study, however, two additional chimpanzees infected with strain HC-TN developed typical acute hepatitis, with peak ALT levels of 296 IU/liter and 90 IU/liter and minimal necroinflammatory changes in liver biopsy samples (FIG. 1). The ALT values were similar to the mean peak ALT of 215±122 IU/liter (mean±standard deviation) observed in >30 chimpanzees acutely infected with other genotype 1 strains (Id.). Thus, it was not possible to confirm that strain HC-TN was more virulent than other strains in chimpanzees.

Virulence depends upon a complex interplay between the virus and the host and may be influenced by the dose of infecting virus, route of entry, and virus sequence, as well as by the immune status of the host. Virus dose or transmission route could have influenced the liver disease in the HC-TN-infected chimpanzees. However, Feinstone et al. (Feinstone, S. M. et al. 1981 *J. Infect. Dis.* 144:588-598) reported that there was no correlation between the infectious HCV dose of the inoculum and the peak ALT among experimentally infected chimpanzees. Furthermore, the course of infection did not differ in animals infected from RNA transcripts and from intravenous inoculation (Bukh, J. et al. 2002 In H. S. Margolis, M. J. Alter, T. J. Liang, and J. L. Dienstag (ed.), Viral hepatitis and liver disease. International Medical Press, Atlanta, Ga.; Major, M. E. et al. 2004 *Hepatology* 39:1709-1720; Major, M. E. et al. 1999 *J. Virol.* 73:3317-3325; Yanagi, M. et al. 1997 *Proc. Natl. Acad. Sci. USA* 94:8738-8743).

Single nucleotide or amino acid changes in a virus genome can result in different levels of virulence, as reported, for example, for an amino acid change in the VP4 region of poliovirus (Bouchard, M. J. et al. 1995 *J. Virol.* 69:4972-4978). It was demonstrated that the ORF sequence of virus recovered at peak viremia from CH1579, with mild hepatitis, was identical to the virus sequence recovered from CH1422, with severe hepatitis. It is possible that the sequences of the poly(U/UC) tract of the 3' UTR, which vary in length and composition among different HCV isolates, differed among the viruses infecting the animals. However, the poly(UC) region of the RNA transcripts used to initiate infection in CH1579 was an exact match with the sequence recovered from CH1422. In fact, the infectious clone of strain HC-TN represents the first true consensus clone of HCV since it did not contain any nucleotide changes, perhaps with the possible exception of the length of the poly(U) stretch of the 3' UTR.

The virus infecting the chimpanzee with severe hepatitis might have had a higher degree of heterogeneity (quasispecies) than those found in the chimpanzees infected with the lowest possible infectious dose and with the monoclonal virus. However, sequence analysis suggested that the virus recovered from the animal with severe hepatitis was very homogeneous. The courses of viral replication during the early acute phase of infection were very similar in the three animals, suggesting that the viruses infecting the chimpanzees had similar replication capacities. It is noteworthy that exposure to low doses of HCV or RNA transcripts from molecular clones, which did not result in detectable infection, were reported to have primed the host immune response in chimpanzees (Kolykhalov, A. A. et al. 2000 *J. Virol.* 74:2046-2051; Shata, M. T. et al. 2003 *Virology* 314:601-616). CH1422, with severe hepatitis, did not have such prior exposure, whereas CH1581 and CH1579, with typical hepatitis, both had such prior exposure. However, the intrahepatic T-cell responses in both of these animals appeared only after about 2 months of active infection. Yet, in CH1579 a weak peripheral T-cell response in the preinoculation samples was detected.

Host immune responses are thought to determine the outcome of HCV infection. Neutralizing antibodies do not appear to play a role in the control of acute HCV in chimpanzees since they do not develop in animals with resolving infection (Bartosch, B. et al. 2003 *Proc. Natl. Acad. Sci. USA* 100:14199-14204; Meunier, J. C. et al. 2005 *Proc. Natl. Acad. Sci. USA* 102:4560-4565). CH1579 did not develop envelope or neutralizing antibodies even though the HC-TN infection resolved (Meunier, J. C. et al. 2005 *Proc. Natl. Acad. Sci. USA* 102:4560-4565). A significant peripheral $CD4^+$ T-cell response occurred much earlier in the animal that cleared the infection (CH1579) than in the animal that became chronically infected (CH1581), suggesting that early priming of the T-cell response may be important to the outcome. A significant response was detected at baseline in CH1579 and thus prior to inoculation, maybe reflecting priming through previous inoculations (see above). Both CH1581 and CH1579 developed HCV-specific intrahepatic antiviral $CD4^+$ and $CD8^+$ T-cell responses; the animal (CH1581) with persistence actually appeared to have an earlier appearance of these responses and in general the strength of these responses was greater than those detected in the animal (CH1579) with acute resolving infection (FIG. 3). However, CH1579 had extraordinarily strong CD4 and CD8 responses at weeks 23 and 33, respectively. It is possible that the intrahepatic $CD8^+$ T-cell response, which was more vigorous during the low-titer period in CH1579 than during the corresponding period in CH1581, was efficient enough to eliminate the virus before escape mutants could establish a robust infection in CH1579, which was not the case with CH1581 (see below). The peripheral CD4+ T-cell response waned soon after viral clearance in CH1579, as did the intrahepatic CD4+ and CD8+ T-cell responses, but they all persisted in the chronically infected animal (CH1581), suggesting that persistence of these responses requires continuous antigen stimulation. It was recently reported that HCV-infected chimpanzees with acute resolving infection had an earlier initial decrease in virus titers than animals that developed a persistent infection (Major, M. E. et al. 2004 *Hepatology* 39:1709-1720). However, the opposite was found with CH1581 and CH1579 (FIG. 1).

One explanation is that differences in virus evolution in response to the host cellular immune response could explain the different outcomes for CH1579 and CH1581. The emergence of escape mutations in T-cell-targeted epitopes has been documented previously for HCV-infected chimpanzees (Erickson, A. L. et al. 2001 *Immunity* 15:883-895; Weiner, A. et al. 1995 *Proc. Natl. Acad. Sci. USA* 92:2755-2759). However, these mutations were not analyzed in the context of coexisting mutations, since only small segments of the genome were sequenced. The cellular immune response against HCV is frequently targeted against multiple epitopes, and escape from a single epitope might not lead to persistence. The entire polyprotein sequence of consecutive samples during the acute infection was analyzed and changes were correlated directly with the host humoral and cellular immune responses. In addition, the possibility of selection of preexisting variants in the chimpanzees studied was limited, since CH1581 was inoculated with the lowest possible infectious dose of polyclonal virus and CH1579 was transfected with RNA transcripts from an infectious clone and thus initially had a monoclonal infection. No mutations were detected in viruses recovered from CH1581 and CH1579 during the first 11 and 13 weeks of follow-up, respectively. In contrast, during the next 7 and 8 weeks of follow-up six and five amino acid changes, respectively were detected. Thus, despite a high rate of replication and an error-prone RNA-dependent RNA polymerase, mutations were not selected until the initial decrease in HCV titers. The accumulation of minor variants might occur during initial replication, and these variants could be selected by means of host immune pressure or replicative advantages, perhaps as second-site changes compensating for decreased replication fitness caused by other changes. Finally, changes might represent random coselected mutations.

Major et al. (Major, M. E. et al. 1999 *J. Virol.* 73:3317-3325) studied the evolution of monoclonal H77 virus, another genotype 1a strain, in two chimpanzees that became persistently infected. Overall, the mutation rates observed for these animals were lower than those for the HC-TN-infected animals. Both animals developed mutations in p7; one of these mutations (M793V) was observed to occur also in the HC-TN-infected animal that became persistently infected. There was only one other common mutation in the two studies, L2456M, which occurred in the HC-TN-infected animal that cleared HCV. Finally, it should be noted that a similar pattern of development of mutations was observed in chimpanzees infected with monoclonal genotype 1b viruses (Bukh, J. et al. 2002 *Proc. Natl. Acad. Sci. USA* 99:14416-14421; Thomson, M. et al. 2001 *Gastroenterology* 121:1226-1233).

Recently, it was found that RNA transcripts from the full-length JFH1 genome (genotype 2a) produced viruses in human liver hepatoma cell lines (Wakita, T. et al. 2005 *Nat. Med.* 11:791-796; Zhong, J. et al. 2005 *Proc. Natl. Acad. Sci. USA* 102:9294-9299). The JFH1 strain was isolated from a patient with fulminant hepatitis, and it has been a question as to whether that fact was related to the unique ability to grow in cell culture. In contrast, wild-type, full-length HC-TN did not replicate in Huh7.5 cells even though it too was isolated from a patient with fulminant hepatitis. The same was reported previously for strain H77, but it was recently reported that a cell-culture-adapted H77 genome could produce viruses in Huh7.5 cells (Yi, M. et al. 2006 *Proc. Natl. Acad. Sci. USA* 103:2310-2315). Given that strains H77 and HC-TN belong to the same HCV subtype and are relatively closely related (FIG. 2), it is possible that these adaptive mutations would also permit replication of the HC-TN strain.

In conclusion, an infectious clone of the HC-TN strain has been developed. The HC-TN sequence was infectious in vivo, but like other infectious clones of HCV genotype 1, this wild-type sequence was not infectious in Huh7-derived cells. The in vivo study of the HC-TN strain demonstrates that virulence of HCV depends primarily upon host responses and not the particular virus strain. The cellular immune response against HCV precedes the initial decrease in virus titer and the development of acute hepatitis. The cellular immune responses did not appear to predict the final outcome of the infection, although differences in timing and magnitude of these responses might have played a role. The emergence of new virus variants, in the absence of neutralizing antibodies, is temporally associated with host cellular immune responses.

What is claimed is:

1. A purified or isolated nucleic acid molecule comprising a hepatitis C virus (HCV) 5' untranslated region (UTR), a sequence that encodes SEQ. ID. NO.: 2, and a HCV 3 'UTR, wherein said nucleic acid produces a HCV that infects chimpanzees.

2. The purified or isolated nucleic acid molecule of claim 1, wherein said molecule comprises SEQ. ID. NO.: 1.

3. The purified or isolated nucleic acid molecule of claim 1, wherein said molecule consists essentially of SEQ. ID. NO.: 1.

4. The purified or isolated nucleic acid molecule of claim 1, wherein said molecule consists of SEQ. ID. NO.: 1.

5. A purified or isolated nucleic acid molecule comprising a sequence that encodes SEQ. ID. NO.: 2.

6. The purified or isolated nucleic acid molecule of claim 5, wherein said sequence comprises SEQ. ID. NO.: 1.

7. The purified or isolated nucleic acid molecule of claim 5, wherein said sequence consists essentially of SEQ. ID. NO.: 1.

* * * * *

SEQUENCE LISTING

```
<160> NUMBER OF SEQ ID NOS: 9

<210> SEQ ID NO 1
<211> LENGTH: 9599
<212> TYPE: DNA
<213> ORGANISM: Hepatitis C virus

<400> SEQUENCE: 1
gccagccccc tgatgggggc gacactccac catgaatcac tccctgtga  ggaactactg      60 tcttcacgca gaaagcgtct agccatggcg ttagtatgag tgtcgtgcag cctccaggac     120 ccccctccc  gggagagcca tagtggtctg cggaaccggt gagtacaccg gaattgccag     180
gacgaccggg tcctttcttg gatcaacccg ctcaatgcct ggagatttgg gcgtgccccc     240
```

```
gcaagactgc tagccgagta gtgttgggtc gcgaaaggcc ttgtggtact gcctgatagg    300
gtgcttgcga gtgccccggg aggtctcgta daccgtgcac catgagcacg aatcctaaac    360
ctcaaagaaa aaccaaacgt aacaccaacc gtcgcccaca ggacgtcaag ttcccgggtg    420
gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcgcgtcg gcccgagggc aggacctggg ctcagcccgg gtacccttgg ccctctatg     600
gcaatgaggg ttgcgggtgg gcgggatggc tcctgtctcc ccgtggctct cggcctagct    660
ggggccccac ggaccccagg cgtaggtcgc gcaatttggg taaggtcatc gatacccta     720
cgtgcggctt cgccgacctc atggggtaca taccgctcgt cggcgcccct cttggaggcg    780
ctgccagggc cctggcgcat ggcgtccggg ttttggaaga cggcgtgaac tatgcaacag    840
ggaaccttcc tggttgctct ttctctattt tccttctggc cctgctctct tgtctgactg    900
gacccgcttc agcctaccaa gtgcgcaact ccacggggct ttaccatgtc accaatgatt    960
gccccaactc gagcattgtg ttcgaggcgg ctgatgccat cctgcacact ccggggtgtg   1020
tcccttgcgt acgcgagggt aacgcctcga ggtgttgggt ggcggtaacc cccacggtgg   1080
ccaccaggga tggcaaactc cccacaacgc agcttcgacg tcacatcgat ctgcttgtcg   1140
ggagcgccac cctctgctcg gcccttacg tgggggacct gtgcgggtct gtctttcttg    1200
ttggtcaact gttcaccttc tctcccaggc gccactggac gacgcaagat tgcaattgtt   1260
ctatctaccc cggccatatt tcaggtcacc gtatggcatg ggatatgatg atgaactggt   1320
cccctacggc ggcgttgttg gtagctcagc tgctccggat cccacaagcc atcctggaca   1380
tgatcgctgg tgctcactgg ggagtcctgg cgggcatggc gtatttctcc atggtgggga   1440
actgggcgaa ggttctggta gtgctgctgc tatttgccgg cgtcgacgcg gaaacctacg   1500
tcaccggggg aagtgccgcc cgtactacgg ctggacttgc tagtcttttc tcaccaggcg   1560
ccaagcagaa catccagctg gtcaacacca acggcagttg gcacatcaat agcacggcct   1620
tgaactgcaa tgacagcctc aacaccggct ggatagcagg acttttctat caccacaaat   1680
tcaactcttc gggctgttcc gagaggttag ccagctgccg accccttacc gattttgccc   1740
agggctgggg ccctatcagt cacgccgacg gaagtggccc cgaccaacgc ccctactgct   1800
ggcactaccc tccaaaaacct tgtggtattg tgcccgcaaa gagcgtgtgt ggcccggtat   1860
attgtttcac tccagtccc gtggtggtgg gaacgaccga caggtcgggc gcgcctacct    1920
acagctgggg tgcaaatgac acggacgtct tcgtccttaa caacaccagg ccaccgctgg   1980
gcaattggtt cggttgcacc tggatgaact caactggatt caccaaagtg tgcggagcgc   2040
cccccttgcgt catcggaggg gtgggcaaca acaccttgcg ctgccccact gattgtttcc   2100
gcaagcatcc ggaagccaca tactctcggt gcggctccgg tcctggatt acgcccaggt    2160
gcctggtcga ctaccgtat aggctttggc attatccttg taccatcaac tacaccgtgt    2220
ttaaagtcag gatgtacgtg ggagggggtcg agcacaggct ggaagctgcc tgcaactgga   2280
cgcgggggcga ccgttgtaat ctggatgaca gggacaggtc cgagctcagc ccgctgctgc   2340
tgtccactac gcagtggcag gtcctcccgt gttccttcac gacccctgcca gccttgtcca   2400
ccggcctcat ccacctccac caaaaacatcg tggacgtgca atacttgtac ggggtgggat   2460
caagcatcgc gtcctgggcc atcaagtggg aatacgtcgt tctcttgttc cttctgcttg   2520
cagacgcgcg cgtctgctcc tgcttgtgga tgatgttact catatcccaa gtggaggcgg   2580
```

```
ctttggagaa cctcgtagta ctcaatgcag catccctggc cgggacacac ggtcttgtat    2640
ccttcctcgt gttcttctgc tttgcatggt atctgaaggg taagtgggtg cccggagcgg    2700
tctacgccct ctacgggatg tggcctctcc tcttgctcct gttagcgttg ccccagcggg    2760
catacgcact ggacacggag gtggccgcgt cgtgtggcgg cgttgttctt gtcgggttaa    2820
tggcgctgac tctgtcacca tattacaagc gctatatcag ctggtgcttg tggtggcttc    2880
agtatttcct gaccagaata gaagcgcaac tgcacgtgtg gattcccccct ctcaacgtcc    2940 gggggggcg cgatgccgtc atcttactca tgtgtgttgt gcacccggct ctggtatttg    3000
acatcaccaa gctactgctg gctgccttcg ggccccttttg gattcttcaa gccagtttgc    3060
ttaaggtacc ctacttcgtg cgcgttcaag gccttctccg gatctgcgcg ctagcgcgga    3120
agatggctgg aggccattac gtgcaaatgg ccatcatcaa gttaggggcg cttactggca    3180
cttatgttta caaccatctc accccccttc gggactgggc gcacaacggc ctgcgagatc    3240
tggccgtggc tgtggagcca gtcgtcttct cccgaatgga gaccaagctt atcacctggg    3300 ggcagacac cgccgcgtgc ggtgacatca tcaacggctt gcccgtctcc gcccggaggg    3360
gccgggagat actgctcggg ccagccgatg gaatggtctc caaggggtgg agattgctgg    3420
cgcccatcac ggcgtacgcc cagcaaacga ggggcctcct agggtgtata atcaccagtc    3480
tgaccggccg ggacaaaaac caagtggagg gtgagatcca gattgtgtca actgctgccc    3540
aaaccttcct ggcaacgtgc atcaacgggg tttgctggac cgtctaccac ggggccggaa    3600
cgaggaccat cgcatcaccc aagggtccgg ttatccaaat gtataccaat gtggacaaag    3660
accttgtggg ctggcccgct cctcaaggtg cccgctcact gacaccctgt acctgcggct    3720
cctcggacct ttacctggtc acgaggcacg ccgatgtcat tcccgtgcgc cggcggggtg    3780
atagcagggg cagcctgctt tcgccccggc ccatttccta cttgaaaggc tcctcgggggg    3840 gtccgctgct gtgccccgcg ggacacgccg taggcttatt cagggccgcg gtgtgcaccc    3900
gtggagtggc taaggcggtg gacttcatcc ctgtggagaa cctagagaca accatgaggt    3960
ccccggtgtt cacggacaac tcctctccac cagcagtgcc ccagagcttc caggtggccc    4020
acctgcatgc tcccaccggc agcggcaaaa gcaccaaggt cccggctgca tacgcagctc    4080
agggctataa ggtgctagtg ctcaacccct ctgtcgctgc aacactgggc tttggtgctt    4140
acatgtccaa ggcccatggg gtcgatccta atatcaggac cggggtgaga acaattacca    4200
ctggcagccc catcacgtac tccacctacg gcaagttcct tgccgacggc gggtgttcag    4260
ggggtgctta tgacataata atttgtgacg agtgccactc cacggatgcc acatccatct    4320
tgggcatcgg caccgttctt gaccaagcag agaccgcggg ggcgagactg gttgtgctcg    4380
ccaccgctac ccctccgggc tccatcaccg tgccccatcc taacatcgag gaggttgctc    4440
tgtccactac cggagagatc cctttttacg gcaaggctat ccccctcgag gcgatcaagg    4500 ggggagaca tctcatcttc tgtcactcaa agaagaagtg cgacgagctc gccgcaaagc    4560
tggtcgcatt gggcatcaat gccgtggcct actaccgcgg tcttgacgtg tctgtcatcc    4620
caaccagcgg cgatgttgtc gtcgtggcga ccgatgctct tatgactggc tataccggcg    4680
actttgactc ggtgatagac tgcaacacgt gtgtcaccca gacagtcgac ttcagccttg    4740
accctacctt caccattgag acgaccacgc tcccccagga cgctgtctcc cgcacacaac    4800
gccggggcag gactggcagg gggaagccag gcatctacag attcgtggca ctgggggagc    4860
gcccctccgg catgttcgac tcgtccgttc tctgtgagtg ctatgacgcg ggctgtgctt    4920
ggtatgagct cacgcccgcc gagactacag ttagactacg agcgtacatg aacaccccgg    4980
```

```
ggctccctgt gtgccaggac catcttgaat tttgggaggg cgtctttaca ggcctcaccc    5040
atatagatgc ccatttccta tctcagacaa agcagagcgg ggaaaacttt ccttacctgg    5100
tagcatacca agcaaccgtg tgcgctaggg ctcaagcccc tcccccatcg tgggaccaga    5160
tgtggaagtg tttgactcgc ctcaagccca ccctccatgg gccaacaccc ttgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtc ggcggcgtcc    5340
tggccgcttt ggccgcgtat tgcctgtcaa caggctgcgt ggtcatagtg ggcaggattg    5400
tcctgtctgg gaagccggca attataccctg acagggaagt tctctaccgg gagttcgatg    5460
agatggaaga gtgctctcag cacttaccgt acatcgagca agggatgatg ctcgccgagc    5520
agttcaagca gaaggccctc ggcctcctgc agaccgcgtc ccgtcaggca gaggttgtcg    5580
cccctgctgt ccagaccaac tggcaaaaac tcgaggcctt ctgggcgaag catatgtgga    5640
acttcatcag tgggatacaa tacttggcgg gcttgtcaac gttgcctggt aaccccgcca    5700
ttgcttcatt gatggctttt acagctgctg tcaccagccc actaaccact agccaaaccc    5760
tcctcttcaa catactgggg gggtgggtgg ctgcccagct tgccgccccc ggtgccgcca    5820
ccgcctttgt gggcgctggc ttagccggcc ccgcaatcgg cagtgttgga ctggggaagg    5880
tcctcgtgga cattctagca gggtatgcgc gggcgtggcg gggagctctt gtagcattca    5940
agatcatgag cggtgaggtc ccctccacgg aggacctagt caacctgctg ccgccatcc    6000 tctcgcctgg agcccttgta gtcggtgtgg tctgcgcagc aatactgcgc cggcacgtcg    6060
gcccgggcga gggggcagtg caatggatga accggctaat cgccttcgcc tcccggggga    6120
accatgtttc ccccacgcac tatgtgccgg agagcgatgc agctgcccgc gtcactacca    6180
tactcagcag cctcactgta acccagctcc tgaggcgact gcaccagtgg ataagctcgg    6240
agtgtaccac tccatgctcc ggttcctggc tgagggacat ctgggactgg atatgcgagg    6300
tgctgagcga ctttaagacc tggctgaaag ccaagctcat gccgcaactg cctgggattc    6360
cctttgtgtc ctgccagcgt gggtataagg gggtctggcg aggggacggc atcatgcaca    6420
ctcgctgcca ctgtggagct gagataactg acatgtcaa aaacgggacg atgaggatcg    6480
ttggtcctaa gacttgcagg aacatgtgga gtgggacttt ccccattaac gcctacacca    6540
cgggcccctg tactccccct cctgcgccga actatacgtt cgcgctgtgg agggtgtctg    6600
cagaggaata cgtggagata aggcaggtgg gggacttcca ctacgtgacg ggtatgacta    6660
ctgacaacct taaatgcccg tgccaggtcc catcgcccga tttttccaca gaattggacg    6720
gggtgcgcct acataggttt gcgccccctt gcaagcccct gctgcgggag gaggtgtcat    6780
tcagagtggg actccacgag tacccggtgg ggtcgcaatt accttgcgag cccgaaccgg    6840
acgtggccgt gttgacgtcc atgctcactg atcctccca taacagca gaggcggccg    6900 ggagaaggtt ggcgagggga tcaccccct ctatggccag ctcctcggct agccaactgt    6960
ccgctccatc tctcagggca acttgcacta ccaaccatga ctcccctgat gctgagctca    7020
tagaggccaa cctcctatgg aggcaggaga tgggcggcaa catcaccagg gttgagtcag    7080
agaacaaagt ggtgattctg gactccttcg atccgcttgt ggcagaggag gatgagcggg    7140
aggtctccgt gcccgcagag atactgcgga agtctcggaa attcacccca gccctaccca    7200
tttgggcgcg gccggactat aacccccgc tggtggagcc gtggaaaaag cctgactacg    7260
aaccacctgt ggtccatggc tgcccgcttc cacctccaca gtccctcct gtgcctccac    7320
```

-continued

```
ctcggaagaa gcggacggtg atcctcaccg aatcaaccct acctactgcc ttggccgagc   7380
ttgccaccaa aagttttggc agctcctcaa cttccggcat tacgggcgac gacacgacaa   7440
catcccctga gcccgcctcc tctagctgcc ctcccgactc cgacgctgag tcctattctt   7500
ccatgccccc tctggagggg gagcctgggg atccggatct cagcgacggg tcatggtcga   7560
cggtcagtag tgaggccgac aaggaggatg tcgtgtgctg ctcaatgtct tatacctgga   7620
caggcgcact cgtcaccccg tgcgccgcgg aagaacaaaa actgcccatc aacgcactaa   7680
gcaactcgtt gctgcgtcat cacaatctgg tgtattccac cacctcacgc agtgcttgcc   7740
aaaggcagaa gaaagtcaca tttgacagac tgcaagtcct ggacagccat taccaggacg   7800
tgctcaagga ggttaaggca gcggcgtcaa aagtgaaggc taacttgcta tccgtagagg   7860
aagcttgcag cctgacgccc ccacactcag ccaaatccaa gtttggctat ggggcaaaag   7920
acgtccgttg ccatgccaga aaggccgtaa accacatcaa ctccgtgtgg aaagaccttc   7980
tggaagacag tgtaacacca atagacacta ccatcatggc taagaacgag gttttctgcg   8040
ttcagcctga aaggggggt cgtaagccag ctcgtctcat cgtgttcccc gacctgggtg   8100
tacgcgtgtg cgagaagatg gccttgtacg acgtagtcag caagctcccc ctagccgtga   8160
tgggaagctc ctacggattc caatactcac caggacagcg ggttgaattc ctcgtgcaag   8220
cgtggaagtc caagaagacc ccaatggggt tttcgtatga tacccgctgt tttgactcca   8280
cagtcactga gaatgatatc cgtacggagg aggcaatcta ccaatgttgt gacctggacc   8340
cccaagcccg cgtggccatc aagtccctca ctgagaggct ttatgtcggg ggccctctta   8400
ccaattcaag gggggagaac tgcggctatc gcaggtgccg cgcgagcggc gtactgacga   8460
ccagctgtgg taacaccctc acctgctaca tcaaggcccg agcagcctgt cgagccgcag   8520
ggctccagga ctgcaccatg ctcgtgtgtg cgacgactt agtcgttatc tgtgagagtg   8580
cgggggtcca ggaggacgcg gcgagcctga gagccttcac ggaggctatg accaggtact   8640
ccgccccccc cggggacccc ccacaaccag aatacgactt ggagctcata acatcatgct   8700
cctccaacgt gtcagtcgcc cacgacggcg ctggaaaaag ggtctactac ctcacccgtg   8760
accctacaac cccctcgcg cgggccgcgt gggagacagc aagacacact ccagtcaatt   8820
cctggctagg caacataatt atgtttgccc ccacactgtg ggcgaggatg atactgatga   8880
cccatttctt tagcgtcctc atagccaggg atcagcttga acaggccctc gattgcgaga   8940
tctacggggc ctgctactcc atagaaccac tggatctacc tccaatcatt caaagactcc   9000
atggcctcag cgcattttca ctccacagtt actctccagg tgaaatcaat agggtggccg   9060
catgcctcag aaaacttggg gtcccgcccc tgcgagcttg agacaccgg gcccggaatg   9120
tccgcgctag gcttctgtcc agaggaggca gggctgccat tgtggcaag tacctcttca   9180
actgggcagt aaggacaaag ctcaaactca ctccaatagc ggccgctggc cggctagact   9240
tatctggctg gttcacggct ggctacagcg ggggagacat ttatcacagc gtgtctcatg   9300
cccggccccg ctggttctgg ttttgcctac tcctgctcgc tgcagggta ggcatctacc   9360
tcctccccaa ccgatgaagg ttggggtaaa cactccggcc tcttaggcca tttcctgttt   9420
tttttttttt tttttttttt tttttttttt tttttttttt tttcttttc cctcttttc   9480
ttctctttt ccttctttaa tggtggctcc atccttagccc tagtcacggc tagctgtgaa   9540
aggtccgtga gccgcatgac tgcagagagt gctgatactg gcctctctgc agatcatgt   9599
```

<210> SEQ ID NO 2
<211> LENGTH: 3011

```
<212> TYPE: PRT
<213> ORGANISM: Hepatitis C virus

<400> SEQUENCE: 2

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
            20                  25                  30

Gly Val Tyr Leu Leu Pro Arg Gly Pro Arg Leu Gly Val Arg Ala
            35                  40                  45

Thr Arg Lys Thr Ser Glu Arg Ser Gln Pro Arg Gly Arg Gln Pro
50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
                100                 105                 110

Arg Arg Arg Ser Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
            130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Gly Pro Ala Ser Ala Tyr
                180                 185                 190

Gln Val Arg Asn Ser Thr Gly Leu Tyr His Val Thr Asn Asp Cys Pro
                195                 200                 205

Asn Ser Ser Ile Val Phe Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
                260                 265                 270

Ser Ala Leu Tyr Val Gly Asp Leu Cys Gly Ser Val Phe Leu Val Gly
            275                 280                 285

Gln Leu Phe Thr Phe Ser Pro Arg Arg His Trp Thr Thr Gln Asp Cys
            290                 295                 300

Asn Cys Ser Ile Tyr Pro Gly His Ile Ser Gly His Arg Met Ala Trp
305                 310                 315                 320

Asp Met Met Met Asn Trp Ser Pro Thr Ala Leu Leu Val Ala Gln
                325                 330                 335

Leu Leu Arg Ile Pro Gln Ala Ile Leu Asp Met Ile Ala Gly Ala His
            340                 345                 350

Trp Gly Val Leu Ala Gly Met Ala Tyr Phe Ser Met Val Gly Asn Trp
            355                 360                 365

Ala Lys Val Leu Val Val Leu Leu Leu Phe Ala Gly Val Asp Ala Glu
            370                 375                 380

Thr Tyr Val Thr Gly Gly Ser Ala Ala Arg Thr Thr Ala Gly Leu Ala
385                 390                 395                 400
```

```
Ser Leu Phe Ser Pro Gly Ala Lys Gln Asn Ile Gln Leu Val Asn Thr
                405                 410                 415

Asn Gly Ser Trp His Ile Asn Ser Thr Ala Leu Asn Cys Asn Asp Ser
            420                 425                 430

Leu Asn Thr Gly Trp Ile Ala Gly Leu Phe Tyr His His Lys Phe Asn
        435                 440                 445

Ser Ser Gly Cys Ser Glu Arg Leu Ala Ser Cys Arg Pro Leu Thr Asp
    450                 455                 460

Phe Ala Gln Gly Trp Gly Pro Ile Ser His Ala Asp Gly Ser Gly Pro
465                 470                 475                 480

Asp Gln Arg Pro Tyr Cys Trp His Tyr Pro Lys Pro Cys Gly Ile
                485                 490                 495

Val Pro Ala Lys Ser Val Cys Gly Pro Val Tyr Cys Phe Thr Pro Ser
                500                 505                 510

Pro Val Val Val Gly Thr Thr Asp Arg Ser Gly Ala Pro Thr Tyr Ser
            515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Arg Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Leu
        595                 600                 605

Val Asp Tyr Pro Tyr Arg Leu Trp His Tyr Pro Cys Thr Ile Asn Tyr
    610                 615                 620

Thr Val Phe Lys Val Arg Met Tyr Val Gly Gly Val Glu His Arg Leu
625                 630                 635                 640

Glu Ala Ala Cys Asn Trp Thr Arg Gly Asp Arg Cys Asn Leu Asp Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Val Glu Ala Ala Leu Glu Asn Leu Val
            740                 745                 750

Val Leu Asn Ala Ala Ser Leu Ala Gly Thr His Gly Leu Val Ser Phe
        755                 760                 765

Leu Val Phe Phe Cys Phe Ala Trp Tyr Leu Lys Gly Lys Trp Val Pro
    770                 775                 780

Gly Ala Val Tyr Ala Leu Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815
```

```
Ser Cys Gly Gly Val Leu Val Gly Leu Met Ala Leu Thr Leu Ser
            820             825             830
Pro Tyr Tyr Lys Arg Tyr Ile Ser Trp Cys Leu Trp Trp Leu Gln Tyr
        835             840             845
Phe Leu Thr Arg Ile Glu Ala Gln Leu His Val Trp Ile Pro Pro Leu
    850             855             860
Asn Val Arg Gly Gly Arg Asp Ala Val Ile Leu Leu Met Cys Val Val
865             870             875             880
His Pro Ala Leu Val Phe Asp Ile Thr Lys Leu Leu Leu Ala Ala Phe
                885             890             895
Gly Pro Leu Trp Ile Leu Gln Ala Ser Leu Leu Lys Val Pro Tyr Phe
            900             905             910
Val Arg Val Gln Gly Leu Leu Arg Ile Cys Ala Leu Ala Arg Lys Met
        915             920             925
Ala Gly Gly His Tyr Val Gln Met Ala Ile Ile Lys Leu Gly Ala Leu
    930             935             940
Thr Gly Thr Tyr Val Tyr Asn His Leu Thr Pro Leu Arg Asp Trp Ala
945             950             955             960
His Asn Gly Leu Arg Asp Leu Ala Val Ala Val Glu Pro Val Val Phe
                965             970             975
Ser Arg Met Glu Thr Lys Leu Ile Thr Trp Gly Ala Asp Thr Ala Ala
            980             985             990
Cys Gly Asp Ile Ile Asn Gly Leu Pro Val Ser Ala Arg Arg Gly Arg
        995             1000            1005
Glu Ile Leu Leu Gly Pro Ala Asp Gly Met Val Ser Lys Gly Trp Arg
    1010            1015            1020
Leu Leu Ala Pro Ile Thr Ala Tyr Ala Gln Gln Thr Arg Gly Leu Leu
1025            1030            1035            1040
Gly Cys Ile Ile Thr Ser Leu Thr Gly Arg Asp Lys Asn Gln Val Glu
                1045            1050            1055
Gly Glu Ile Gln Ile Val Ser Thr Ala Ala Gln Thr Phe Leu Ala Thr
            1060            1065            1070
Cys Ile Asn Gly Val Cys Trp Thr Val Tyr His Gly Ala Gly Thr Arg
        1075            1080            1085
Thr Ile Ala Ser Pro Lys Gly Pro Val Ile Gln Met Tyr Thr Asn Val
    1090            1095            1100
Asp Lys Asp Leu Val Gly Trp Pro Ala Pro Gln Gly Ala Arg Ser Leu
1105            1110            1115            1120
Thr Pro Cys Thr Cys Gly Ser Ser Asp Leu Tyr Leu Val Thr Arg His
                1125            1130            1135
Ala Asp Val Ile Pro Val Arg Arg Arg Gly Asp Ser Arg Gly Ser Leu
            1140            1145            1150
Leu Ser Pro Arg Pro Ile Ser Tyr Leu Lys Gly Ser Ser Gly Gly Pro
        1155            1160            1165
Leu Leu Cys Pro Ala Gly His Ala Val Gly Leu Phe Arg Ala Ala Val
    1170            1175            1180
Cys Thr Arg Gly Val Ala Lys Ala Val Asp Phe Ile Pro Val Glu Asn
1185            1190            1195            1200
Leu Glu Thr Thr Met Arg Ser Pro Val Phe Thr Asp Asn Ser Ser Pro
                1205            1210            1215
Pro Ala Val Pro Gln Ser Phe Gln Val Ala His Leu His Ala Pro Thr
            1220            1225            1230
Gly Ser Gly Lys Ser Thr Lys Val Pro Ala Ala Tyr Ala Ala Gln Gly
```

-continued

```
            1235                1240                1245
Tyr Lys Val Leu Val Leu Asn Pro Ser Val Ala Thr Leu Gly Phe
1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Ala Tyr Asp Ile
                1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
        1330                1335                1340

Val Leu Ala Thr Ala Thr Pro Pro Gly Ser Ile Thr Val Pro His Pro
1345                1350                1355                1360

Asn Ile Glu Glu Val Ala Leu Ser Thr Thr Gly Glu Ile Pro Phe Tyr
                1365                1370                1375

Gly Lys Ala Ile Pro Leu Glu Ala Ile Lys Gly Gly Arg His Leu Ile
                1380                1385                1390

Phe Cys His Ser Lys Lys Lys Cys Asp Glu Leu Ala Ala Lys Leu Val
            1395                1400                1405

Ala Leu Gly Ile Asn Ala Val Ala Tyr Tyr Arg Gly Leu Asp Val Ser
        1410                1415                1420

Val Ile Pro Thr Ser Gly Asp Val Val Val Ala Thr Asp Ala Leu
1425                1430                1435                1440

Met Thr Gly Tyr Thr Gly Asp Phe Asp Ser Val Ile Asp Cys Asn Thr
                1445                1450                1455

Cys Val Thr Gln Thr Val Asp Phe Ser Leu Asp Pro Thr Phe Thr Ile
            1460                1465                1470

Glu Thr Thr Thr Leu Pro Gln Asp Ala Val Ser Arg Thr Gln Arg Arg
            1475                1480                1485

Gly Arg Thr Gly Arg Gly Lys Pro Gly Ile Tyr Arg Phe Val Ala Leu
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
                1525                1530                1535

Val Arg Leu Arg Ala Tyr Met Asn Thr Pro Gly Leu Pro Val Cys Gln
            1540                1545                1550

Asp His Leu Glu Phe Trp Glu Gly Val Phe Thr Gly Leu Thr His Ile
        1555                1560                1565

Asp Ala His Phe Leu Ser Gln Thr Lys Gln Ser Gly Glu Asn Phe Pro
        1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Thr Arg Leu Lys Pro
                1605                1610                1615

Thr Leu His Gly Pro Thr Pro Leu Leu Tyr Arg Leu Gly Ala Val Gln
                1620                1625                1630

Asn Glu Val Thr Leu Thr His Pro Ile Thr Lys Tyr Ile Met Thr Cys
            1635                1640                1645

Met Ser Ala Asp Leu Glu Val Val Thr Ser Thr Trp Val Leu Val Gly
1650                1655                1660
```

-continued

```
Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
            1685                1690                1695

Asp Arg Glu Val Leu Tyr Arg Glu Phe Asp Glu Met Glu Glu Cys Ser
            1700                1705                1710

Gln His Leu Pro Tyr Ile Glu Gln Gly Met Met Leu Ala Glu Gln Phe
            1715                1720                1725

Lys Gln Lys Ala Leu Gly Leu Leu Gln Thr Ala Ser Arg Gln Ala Glu
            1730                1735                1740

Val Val Ala Pro Ala Val Gln Thr Asn Trp Gln Lys Leu Glu Ala Phe
1745                1750                1755                1760

Trp Ala Lys His Met Trp Asn Phe Ile Ser Gly Ile Gln Tyr Leu Ala
            1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Ser Gln Thr Leu Leu
            1795                1800                1805

Phe Asn Ile Leu Gly Gly Trp Val Ala Ala Gln Leu Ala Ala Pro Gly
            1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Val Asp Ile Leu Ala Gly Tyr Gly
            1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
            1875                1880                1885

Pro Gly Ala Leu Val Val Gly Val Val Cys Ala Ala Ile Leu Arg Arg
            1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
            1925                1930                1935

Glu Ser Asp Ala Ala Ala Arg Val Thr Thr Ile Leu Ser Ser Leu Thr
            1940                1945                1950

Val Thr Gln Leu Leu Arg Arg Leu His Gln Trp Ile Ser Ser Glu Cys
            1955                1960                1965

Thr Thr Pro Cys Ser Gly Ser Trp Leu Arg Asp Ile Trp Asp Trp Ile
            1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Lys
            2005                2010                2015

Gly Val Trp Arg Gly Asp Gly Ile Met His Thr Arg Cys His Cys Gly
            2020                2025                2030

Ala Glu Ile Thr Gly His Val Lys Asn Gly Thr Met Arg Ile Val Gly
            2035                2040                2045

Pro Lys Thr Cys Arg Asn Met Trp Ser Gly Thr Phe Pro Ile Asn Ala
            2050                2055                2060

Tyr Thr Thr Gly Pro Cys Thr Pro Leu Pro Ala Pro Asn Tyr Thr Phe
2065                2070                2075                2080
```

```
Ala Leu Trp Arg Val Ser Ala Glu Glu Tyr Val Glu Ile Arg Gln Val
                2085                2090                2095

Gly Asp Phe His Tyr Val Thr Gly Met Thr Thr Asp Asn Leu Lys Cys
                2100                2105                2110

Pro Cys Gln Val Pro Ser Pro Glu Phe Phe Thr Glu Leu Asp Gly Val
                2115                2120                2125

Arg Leu His Arg Phe Ala Pro Pro Cys Lys Pro Leu Leu Arg Glu Glu
                2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
                2180                2185                2190

Gly Ser Pro Pro Ser Met Ala Ser Ser Ser Ala Ser Gln Leu Ser Ala
                2195                2200                2205

Pro Ser Leu Arg Ala Thr Cys Thr Thr Asn His Asp Ser Pro Asp Ala
                2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
                2245                2250                2255

Asp Pro Leu Val Ala Glu Glu Asp Glu Arg Glu Val Ser Val Pro Ala
                2260                2265                2270

Glu Ile Leu Arg Lys Ser Arg Lys Phe Thr Pro Ala Leu Pro Ile Trp
                2275                2280                2285

Ala Arg Pro Asp Tyr Asn Pro Pro Leu Val Glu Pro Trp Lys Lys Pro
                2290                2295                2300

Asp Tyr Glu Pro Pro Val Val His Gly Cys Pro Leu Pro Pro Pro Gln
2305                2310                2315                2320

Ser Pro Pro Val Pro Pro Pro Arg Lys Lys Arg Thr Val Ile Leu Thr
                2325                2330                2335

Glu Ser Thr Leu Pro Thr Ala Leu Ala Glu Leu Ala Thr Lys Ser Phe
                2340                2345                2350

Gly Ser Ser Ser Thr Ser Gly Ile Thr Gly Asp Asp Thr Thr Thr Ser
                2355                2360                2365

Pro Glu Pro Ala Ser Ser Ser Cys Pro Pro Asp Ser Asp Ala Glu Ser
                2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Ser Glu Ala Asp Lys Glu Asp
                2405                2410                2415

Val Val Cys Cys Ser Met Ser Tyr Thr Trp Thr Gly Ala Leu Val Thr
                2420                2425                2430

Pro Cys Ala Ala Glu Glu Gln Lys Leu Pro Ile Asn Ala Leu Ser Asn
                2435                2440                2445

Ser Leu Leu Arg His His Asn Leu Val Tyr Ser Thr Thr Ser Arg Ser
                2450                2455                2460

Ala Cys Gln Arg Gln Lys Lys Val Thr Phe Asp Arg Leu Gln Val Leu
2465                2470                2475                2480

Asp Ser His Tyr Gln Asp Val Leu Lys Glu Val Lys Ala Ala Ala Ser
                2485                2490                2495

Lys Val Lys Ala Asn Leu Leu Ser Val Glu Glu Ala Cys Ser Leu Thr
```

-continued

```
                2500                2505                2510
Pro Pro His Ser Ala Lys Ser Lys Phe Gly Tyr Gly Ala Lys Asp Val
        2515                2520                2525
Arg Cys His Ala Arg Lys Ala Val Asn His Ile Asn Ser Val Trp Lys
        2530                2535                2540
Asp Leu Leu Glu Asp Ser Val Thr Pro Ile Asp Thr Ile Met Ala
2545                2550                2555                2560
Lys Asn Glu Val Phe Cys Val Gln Pro Glu Lys Gly Arg Lys Pro
        2565                2570                2575
Ala Arg Leu Ile Val Phe Pro Asp Leu Gly Val Arg Val Cys Glu Lys
        2580                2585                2590
Met Ala Leu Tyr Asp Val Val Ser Lys Leu Pro Leu Ala Val Met Gly
        2595                2600                2605
Ser Ser Tyr Gly Phe Gln Tyr Ser Pro Gly Gln Arg Val Glu Phe Leu
        2610                2615                2620
Val Gln Ala Trp Lys Ser Lys Lys Thr Pro Met Gly Phe Ser Tyr Asp
2625                2630                2635                2640
Thr Arg Cys Phe Asp Ser Thr Val Thr Glu Asn Asp Ile Arg Thr Glu
        2645                2650                2655
Glu Ala Ile Tyr Gln Cys Cys Asp Leu Asp Pro Gln Ala Arg Val Ala
        2660                2665                2670
Ile Lys Ser Leu Thr Glu Arg Leu Tyr Val Gly Gly Pro Leu Thr Asn
        2675                2680                2685
Ser Arg Gly Glu Asn Cys Gly Tyr Arg Arg Cys Arg Ala Ser Gly Val
        2690                2695                2700
Leu Thr Thr Ser Cys Gly Asn Thr Leu Thr Cys Tyr Ile Lys Ala Arg
2705                2710                2715                2720
Ala Ala Cys Arg Ala Ala Gly Leu Gln Asp Cys Thr Met Leu Val Cys
        2725                2730                2735
Gly Asp Asp Leu Val Val Ile Cys Glu Ser Ala Gly Val Gln Glu Asp
        2740                2745                2750
Ala Ala Ser Leu Arg Ala Phe Thr Glu Ala Met Thr Arg Tyr Ser Ala
        2755                2760                2765
Pro Pro Gly Asp Pro Pro Gln Pro Glu Tyr Asp Leu Glu Leu Ile Thr
        2770                2775                2780
Ser Cys Ser Ser Asn Val Ser Val Ala His Asp Gly Ala Gly Lys Arg
2785                2790                2795                2800
Val Tyr Tyr Leu Thr Arg Asp Pro Thr Thr Pro Leu Ala Arg Ala Ala
        2805                2810                2815
Trp Glu Thr Ala Arg His Thr Pro Val Asn Ser Trp Leu Gly Asn Ile
        2820                2825                2830
Ile Met Phe Ala Pro Thr Leu Trp Ala Arg Met Ile Leu Met Thr His
        2835                2840                2845
Phe Phe Ser Val Leu Ile Ala Arg Asp Gln Leu Glu Gln Ala Leu Asp
        2850                2855                2860
Cys Glu Ile Tyr Gly Ala Cys Tyr Ser Ile Glu Pro Leu Asp Leu Pro
2865                2870                2875                2880
Pro Ile Ile Gln Arg Leu His Gly Leu Ser Ala Phe Ser Leu His Ser
        2885                2890                2895
Tyr Ser Pro Gly Glu Ile Asn Arg Val Ala Ala Cys Leu Arg Lys Leu
        2900                2905                2910
Gly Val Pro Pro Leu Arg Ala Trp Arg His Arg Ala Arg Asn Val Arg
        2915                2920                2925
```

-continued

```
Ala Arg Leu Leu Ser Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                2960

Ala Ala Gly Arg Leu Asp Leu Ser Gly Trp Phe Thr Ala Gly Tyr Ser
            2965                2970                2975

Gly Gly Asp Ile Tyr His Ser Val Ser His Ala Arg Pro Arg Trp Phe
            2980                2985                2990

Trp Phe Cys Leu Leu Leu Ala Ala Gly Val Gly Ile Tyr Leu Leu
        2995                3000                3005

Pro Asn Arg
    3010

<210> SEQ ID NO 3
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 3
cgcaaccctc attgccatag                                                      20

<210> SEQ ID NO 4
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 4
ctcgaggttg cgaccgctcg gaag                                                 24

<210> SEQ ID NO 5
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 5
cggggtacca cgatctgacc gccacccggg aac                                       33

<210> SEQ ID NO 6
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 6
tggttcacgg ctggctacag                                                      20

<210> SEQ ID NO 7
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 7
cagcggggga gacatttatc acag                                                 24
```

-continued

```
<210> SEQ ID NO 8
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 8
cacagcgtgt ctcatgcccg gccc                                            24

<210> SEQ ID NO 9
<211> LENGTH: 35
<212> TYPE: RNA
<213> ORGANISM: Hepatitis C virus

<400> SEQUENCE: 9
cuuuuucccu cuuuuucuuc ucuuuuuccu ucuuu                                35
```